United States Patent [19]

DeBarbieri et al.

[11] Patent Number: 4,740,501

[45] Date of Patent: * Apr. 26, 1988

[54] INTERFERENCE OF B-TYPE RETROVIRUS REPLICATION WITH A TRIPEPTIDE COMPOUND

[76] Inventors: Augusto DeBarbieri, Via Morosini 36, Milano, Italy; Julius G. Bekesi, 493 Warwick Ave., Teaneck, N.J. 07666

[*] Notice: The portion of the term of this patent subsequent to Sep. 10, 2002 has been disclaimed.

[21] Appl. No.: 711,830

[22] Filed: Mar. 14, 1985

Related U.S. Application Data

[63] Continuation-in-part of Ser. No. 654,477, Sep. 26, 1984, abandoned, which is a continuation-in-part of Ser. No. 621,796, Jun. 18, 1984, Pat. No. 4,540,683, which is a continuation-in-part of Ser. No. 468,036, Feb. 23, 1983, Pat. No. 4,508,710, which is a continuation-in-part of Ser. No. 455,477, Jan. 4, 1983, abandoned, which is a continuation-in-part of Ser. No. 311,646, Oct. 15, 1981, Pat. No. 4,428,875, which is a continuation-in-part of Ser. No. 173,621, Jul. 30, 1980, Pat. No. 4,314,999, which is a continuation-in-part of Ser. No. 929,237, Jul. 31, 1978, Pat. No. 4,216,208.

[51] Int. Cl.$^4$ .................... A61K 37/02; C12N 5/02
[52] U.S. Cl. ............................. 514/18; 514/19; 530/331; 435/240.2; 435/240.21
[58] Field of Search .................. 514/18, 19; 530/331; 435/240.2, 240.21

[56] References Cited

U.S. PATENT DOCUMENTS

| | | | |
|---|---|---|---|
| 4,087,520 | 5/1978 | Bran et al. | 514/18 |
| 4,127,534 | 11/1978 | Coy et al. | 514/18 |
| 4,153,688 | 5/1979 | Demecoli et al. | 514/18 |
| 4,540,683 | 9/1985 | DeBarbieri et al. | 514/18 |

*Primary Examiner*—Blondel Hazel
*Attorney, Agent, or Firm*—Fisher, Christen & Sabol

[57] ABSTRACT

The cancericidal activity of all the permutations of a tripeptide compound formed from dichlorodiethylaminophenylalanine, parafluorophenylalanine and methionine bonded together with peptide links was demonstrated using seven in vitro tumor cell lines. The viabilities of each of the tumor cell lines were significantly reduced by treatment for 1 to 24 hours with 1 to 50 ug of the tripeptide per ml of carrier solvent. A pulse exposure to the tripeptide demonstrated that the reductions in tumor cell was comparable to continuous exposure. Other in vitro tests were all conducted on AKR mice.

Method of treating virus by exposing the virus to one of the noted tripeptides compounds is also contemplated.

Methods of treating tumor cells with the tripeptides dissolved in a solvent consisting of dimethylacetamide, propylene glycol and absolute ethanol are also contemplated by the present invention.

Methods of treating tumor cells resistant to other chemotherapeutic agents is contemplated by this invention.

Methods of treating mouse mammary tumor cells to reduce production of the B-type retrovirus, mouse mammary tumor virus (MMTV), is contemplated by this invention.

7 Claims, 15 Drawing Sheets

INTERFERENCE OF B-TYPE RETROVIRUS REPLICATION WITH A TRIPEPTIDE COMPOUND

RELATED APPLICATIONS

This application is a continuation-in-part of copending application U.S. Ser. No. 654,447, filed Sept. 26, 1984 now abandoned; which is a continuation-in-part of copending application U.S. Ser. No. 621,796, filed June 18, 1984; now U.S. Pat. No. 4,540,683; which is a continuation-in-part of copending U.S. Ser. No. 468,036, filed Feb. 23, 1983 now U.S. Pat. No. 4,508,710, which is a continuation-in-part of U.S. application Ser. No. 455,477, filed Jan. 4, 1983, now abandoned; which is a continuation-in-part of U.S. application Ser. No. 311,646, filed Oct. 15, 1981, now U.S. Pat. No. 4,428,875, which is a continuation-in-part of U.S. application Ser. No. 173,621, filed July 30, 1980, now U.S. Pat. No. 4,314,999; which is a continuation-in-part of application Ser. No. 929,237, filed July 31, 1978, now U.S. Pat. No. 4,216,208.

BACKGROUND OF THE INVENTION

1. Field of the Invention

The present invention relates to methods of treating different types of cancer cells either in vitro or in vivo by treatment with a tripeptide in which the amino acid dichlorodiethylaminophenylalanine is bonded by peptide links to parafluorophenylalanine and methionine.

2. Prior Art

Chemotherapy has been and still is an object of intense research. Certain positive results have undoubtedly been achieved, especially by means of polychemotherapy realized byassociating different active substances according to carefully developed protocols. However, the ideal therapy has not been found. The need to find new active substances has been particularly emphasized. All the foregoing justifies continuous research directed toward preparing new chemotherapeutic compounds active against cancerous tumors. There are already known peptides having anti-tumor activity, consisting of both normal and antimetabolic amino acids, coupled by means of a peptide bond. Such peptides have for years been in therapeutic use with favorable results both in monochemotherapy and in polychemotherapy.

As disclosed in copending U.S. application Ser. No. 311,646, a new family of antitumor compounds is characterized in that each compound comprises the amino acids dichlorodiethylaminophenylalanine, parafluorophenylalanine and methionine bonded together by CO—NH peptide links formed by the respective amino and carboxyl groups of the said amino acids. All possible permutations of the three amino acids are set forth as follows:

1. pFPne. MPhe. Met
2. pFPhe. Met. MPhe
3. MPhe. pFPhe. Met
4. MPhe. Met. p.FPhe
5. Met. pFPhe. MPhe
6. Met. MPhe. p.FPhe wherein "MPhe" indicates the amino acid dichlorodiethylaminophenylalanine having the structural formula:

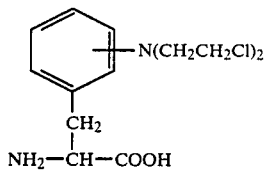

and wherein "pFPhe" indicates the amino acid parafluorophenylalanine having the structural formula:

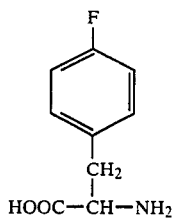

and wherein "Met" indicates the amino acid methionine having the structural formula:

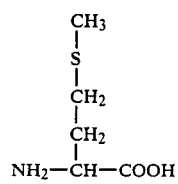

The above-identified tripeptides are useful in the treatment of malignant tumors. The above noted tripeptides are prepared by condensing one of the amino acids having a blocked amine group with another of said amino acids having a blocked carboxyl group with the aid of dicyclohexylcarbodiimide; removing one of the blocking groups to form a dipeptide having a blocked amine or carboxyl group; and condensing the dipeptide with the third amino acid to form the tripeptide with the aid of dicyclohexylcarbodiimide. Compounds of the tripeptide can also be formed, such as compound, by esterifying the tripeptide; and introducing hydrogenchloride.

To further illustrate the synthesis of a tripeptide compound, the following specific process is set forth.

CHEMICAL SYNTHESIS

Synthesis of 3-(p-fluorophenyl)-L-alanyl-3-[m-bis(2-chloroethyl)aminophenyl]-L-alanine ethyl ester. Depeptide I by Reaction I

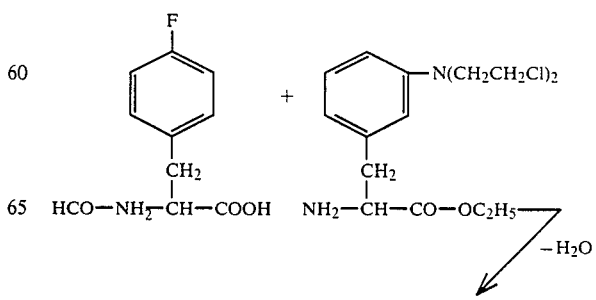

-continued

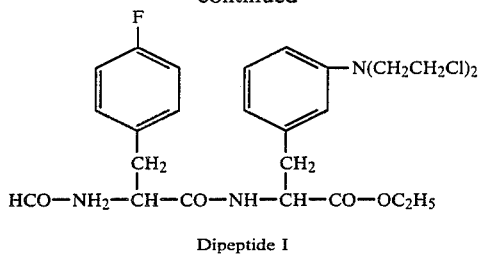

Dipeptide I

To m-bis(2-chloroethyl)aminophenyl-L-alanine ethyl ester [25.88 g] in 150 ml of tetrahydrofuran [15.37 g°], 3-(p-fluorophenyl)L-alanine [17.18 g] and of N,N-dicyclohexylcarbodiimide (coupling agent) [15.85 g] were added successively while stirring for 15 minutes at 0° C. Temperature was then allowed to rise to 20° C. and the reaction mixture was held at this condition for 5 hours. At the completion of the reaction, dicyclohexylurea was removed by filtration and the filtrate was evaporated at 40° C. at a reduced pressure. Residue then was recovered by adding ethyl ether (150 ml) and the precipitate was recovered by filtration, and vacuum dried at 40° C. The raw substance was further purified by crystallization in 96% ethyl alcohol yielding a white crystalline substance (Dipeptide I) with Mp 126°-7° C. Analysis showed a molecular composition of $C_{25}H_{30}FCl_2N_3O_4$ (M=526.44). The calculated molecular composition of the substance in %: C 57.04 -H 5.74 -N 7.98 -Cl 13.47; and found %: C 56.88 -H 5.71 -N 8.01 -Cl 13.32. The overall yield of the reaction was 73% Dipeptide I.

Synthesis of
3-(p-fluorophenyl)-L-alanyl-3-[m-bis(2-chloroethyl)aminophenyl]-L-alanine. Dipeptide II by Reaction II

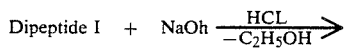

-continued

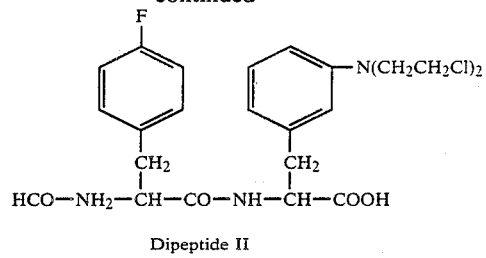

Dipeptide II

The white crystalline substance [26.3 g] (Dipeptide I) from Reaction I was dissolved in acetone [130 ml] by gently heating at 40° C. After cooling it to room temperature, 50 ml of 1N NaOH was added while stirring for 1 hour at 20° C. The hydrolysis reaction was monitored with TLC using a mixture of ethyl alcohol/ethyl acetate/acetic acid: 50:50:1 (v/v/v) solvent system. At the completion of reaction, 50 ml of 1N HCl were slowly added. The white precipitate (Dipeptide II) thus formed was separated by filtration and washed with water until disappearance of Cl from the filtrate. The thus obtained substance was first air dried then vacuum dried. The white amorphous substance had the following characteristics: MP 203°-206° C., a molecular composition of $C_{23}H_{26}FCl_2N_3O_4$ (M=498.39). The calculated composition in %: C 55.43 -H 5.26 -N 8.43 -Cl 14.23, found %: C 55.17 -H 5.24 -N 8.47 -Cl 14.81. The yield of Reaction II was 95% of Dipeptide II.

Synthesis of
3-(p-fluorophenyl)-L-alanyl-3-[m-bis(2-chloroethyl)aminophenyl]-L-alanyl-L-methionine ethyl ester.
Tripeptide III by Reaction III

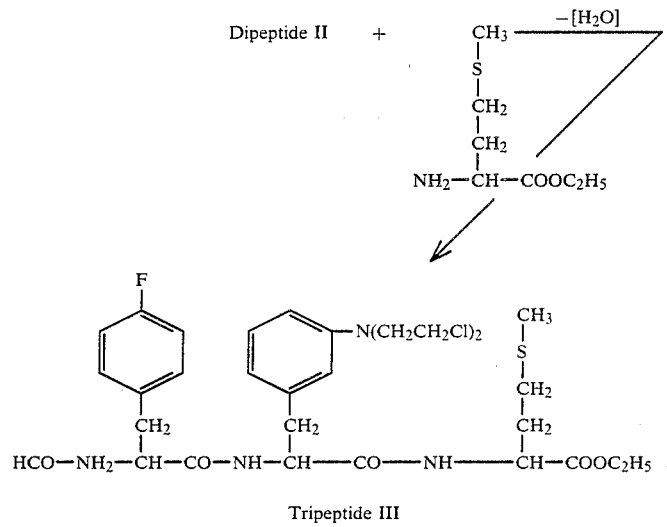

Tripeptide III

Dipeptide II (27.7 g) derived from reaction II was dissolved in 225 ml of N,N-dimethylformamide at 40° C. After cooling it to 15° C., a solution of L-methionine ethyl ester [10.28 g] in 20 ml of N,N-dimethylformamide was added, followed by successive addition of N-hydroxysuccinimide [8.6 g] and N,N-dicyclohexylcarbodiimide [12.57 g] in 25 ml of N,N-dimethylformamide. The thus obtained mixture was held at 5° C. for 30 minutes while stirring. Then the temperature was allowed to rise to 20° C. Dicyclohexylurea was removed by filtration, and to the filtrate while stirring, 1800 ml of water was added at 15° C. After washing, the filtrate was air dried and then successively kept under vacuum in the presence of $P_2O$ at 40° C. Purification of the crude substance was achieved by suspending it in 120 ml of absolute ethyl alcohol and solubilized by adding small portions of N,N-dimethylformamide and suspended for 15 hours at 5° C. The crystalline product was filtered and washed with absolute ethyl alcohol and dried under vacuum at 40° C. The white crystalline substance, Tripeptide III and the following properties: MP 187°–189° C., an analysis showing $C_{30}H_{39}FCl_2N_4O_5S$ (M=657.64), with-calculated composition (%) C 54.79 -H 5.98 -N 8.51 -Cl 10.78 -S 4.87. Found (%): C 54.03 -H 5.89 -N 8.52 -Cl 10.71 -S 4.84.

Synthesis of
3-(p-fluorophenyl)-L-alanyl-3-[m-bis(2-chloroethyl)aminophenyl]-L-alanyl-L-methionine ethyl ester HCl.
Tripeptide IV compound by Reaction IV

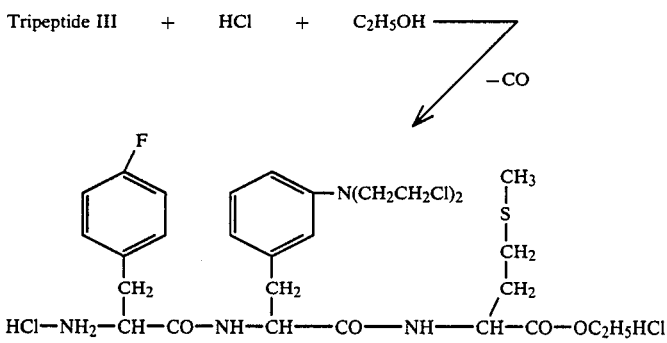

Tripeptide III [17.75 g] from Reaction III was suspended in 250 ml HCl solution (4.1% w/v) in absolute ethyl alcohol and was stirred for 4 hours at 20° C. The reaction mixture was held for 15 hours at 5° C. The course of hydrolysis reaction was monitored with TLC using ethyl ester/acetic acid/water=135:27:9 (v/v/v) solvent system. At the completion of the reaction, to the resulting clear solution 250 ml of water were slowly added while stirring and maintaining the pH at 3–3.2 with $NaHCO_3$ at 5° C. After 20 minutes agitation, the white bulky substance was filtered followed by washing with cold water at 5° C. The sample was first air dried, then vacuum dried at 40° C. in the presence of $P_2O_5$. Purification of the crude product was performed. Crystallization in isopropyl alcohol at 60°–65° C. was conducted after which the product in the isopropyl alcohol was cooled for 16 hours, at 15° C., filtered, washed first with isopropyl alcohol, then with acetone and dried under vacuum at 40° C. for 8 hours. The analysis of the resulting white crystalline substance (the tripeptide compound) showed the following characteristics MP 180°–182° C.; Analysis: for $C_{29}H_{39}Cl_2FN_4O_4S$ HCl (MW=666.08); Calculated %: C 52.29-H 6.05-N 8.41-Cl 15.97-S 4.81; Found %: C 52.31-H 6.09-H 8.38-Cl 15.85-S 4.76.

Retroviruses are ubiquitous in nature and are the etiologic agents of mammary tumors and leukemia/lymphoma in rodents and other mammals, including primates. Previous investigations of the therapeutic efficacy of drugs against these retrovirus tumor models have indicated that many agents capable of eliminating tumor cells had limited or no effect on retrovirus replication. Consequently, viral induced reinduction of the disease occurred at a later time despite initial elimination of neoplastic cells. Similar retrovirus particles and related cellular transforming genes have been detected in human cancer tissue. Although their causative role in human cancer has yet to be established, evidence associating retroviruses such as the human T-cell leukemia virus (HTLV) and the c-onc genes homologous to retrovirus genes with human cancer tissue has ceen accumulating. The presence of these retroviruses and related genetic material in human neoplasia suggests that a possible adjunct to effective chemotherapy would be the inclusion of antiviral agents.

It is an object of this invention to provide a method for treating retroviruses by interfering with viral replication.

SUMMARY OF THE INVENTION

All six of the specific tripeptide compounds have similar characteristics and results in treating malignant tumor cells as well as viruses. For the purpose of simplification, only the tripeptide compound set forth previously in the chemical synthesis, is employed with regard to the remaining disclosure.

This invention is a method for interfering with B-type retrovirus replication comprising the exposing of host cells infected by the virus to a therapeutically effective dose of a tripeptide compound, the tripeptide compound has amino acid members selected from the group consisting of:

(a) 3-(p-fluorophenyl)-L-alanyl-3[m-bis(2-chloroethyl)-aminophenyl]-L-alanyl-L-methionine
(b) 3-[m-bis(2-chloroethyl)aminophenyl]-L-alanyl-3-(p-fluorophenyl)-L-alanyl-L-methionine
(c) 3-(p-fluorophenyl)-L-alanyl-L-methionyl-3-[m-bis(2-chloroethyl)aminophenyl]-L-alanine
(d) 3-[m-bis(2-chloroethyl)aminophenyl]-L-alanyl-L-methionyl-3-(p-fluorophenyl)-L-alanine
(e) L-methionyl-3-(p-fluorophenyl)-L-alanyl-3-[m-bis(2-chloroethyl)aminophenyl]-L-alanine
(f) L-methionyl-3-[m-bis(2-chloroethyl)aminophenyl]-L-alanyl-3-(p-fluorophenyl)-L-alanine.

The therapeutically effective dose of the tripeptide compound is below the toxic or lethal dose for the majority of the host cells.

DETAILED DESCRIPTION OF THE EMBODIMENTS

IN VITRO PREPARATION

Figure 1:
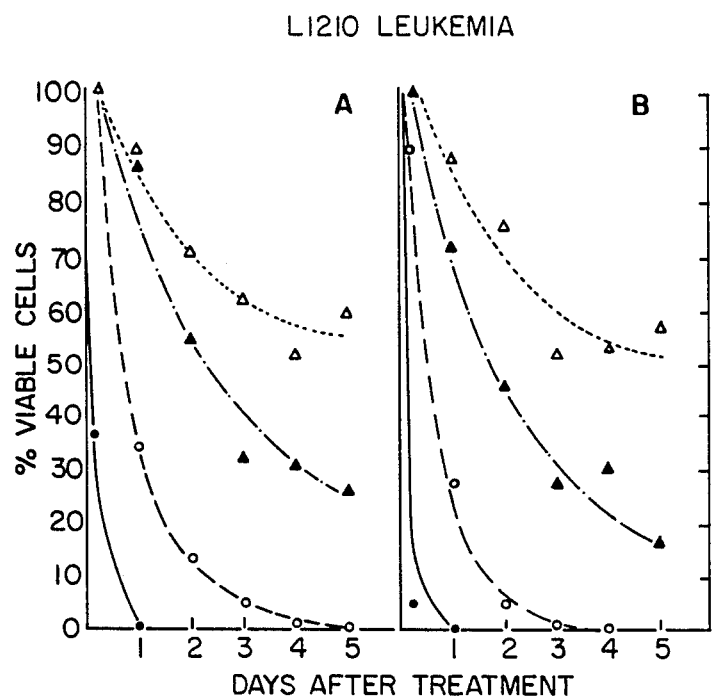
FIG. 1 shows survival of L-1210 leukemia suspensions following a 30 min (A) or 1 hr (B) pulse exposure to 1 (Δ . . . Δ), 5(▲-▲), 10 (o - - o) and 25 (● - ●) ug of the tripeptide/ml of carrier solvent. L-1210 cell suspensions contained $6 \times 10^5$ cells/ml at the time of treatment and the range of viable control cells during the 5-day observation period was $6.5$-$10 \times 10^5$ cells/ml.

The preparation for the in vitro analysis of the tumor cells is as follows: The murine mammary tumor cell line, MJY-alpha, was derived from adenocarcinomas induced in BALB/cfC3H females as a result of infection and oncogenesis by the mouse mammary tumor virus (MMTV). The epithelioid cell line was tumorigenic in syngenic BALB/c hosts and was used between the 25th and 65th in vitro subcultures. Growth medium was RPMI medium No. 1640 supplemented with 18% fetal calf serum, 10 uM bovine insulin, penicillin (250 U/ml) and streptomycin (100 ug/ml). Also, 13.8 uM hydrocortisone was included 24 hours prior to viral harvests.

B-16 melanoma cell cultures were established from the transplantable B-16 tumor line passaged subcutaneously in male, C57BL/6Jx mice. Melanomas from 3 to 5 mice were finely minced, washed three times with serum-free growth medium and cultured as explants using Minimal Essential Medium containing D-valine and Earle's compounds supplemented with 20% calf serum and antibiotics. Confluent primary explant cultures were subsequently passaged weekly as single cell suspensions using a solution of STV. Two, 4 to 12 month old B-16 cell cultures initiated in this manner were used between their 13th to 45th in vitro passages. Both in vitro lines of B-16 cells contained melanized cells and were tumorigenic in syngenic mice.

Primary L-1210 leukemia suspension cultures were initiated from the virulent, in vivo ascites line maintained in DBA/2 Ba mice or their F$_1$ hybrid, BDf$_1$ (BALB/c×DBA/2). L-1210 cells were harvested by washing the peritoneal cavity of tumor-bearing mice with physiological saline (0.85% NaCl, pH 7.2) containing 5% heparin (v/v) without preservatives. Leukemic cells were separated on Ficoll-Hypaque gradients followed by several washes in 0.01M phosphate-buffered saline, pH 7.4. Tumor cell preparations were consistently free of erythrocytes, and 98% of the L-1210 cell population excluded trypan blue. Suspension cultures were initiated and maintained in RPMI medium No. 1630 containing 10% fetal calf serum and antibiotics.

The Epstein Barr Virus infected human, B-lymphoma cell lines; Raji and P$_3$HR-1 were cultured as suspensions in RPMI medium No. 1640 supplemented with 10% heat inactivated fetal calf serum, penicillin (250 U/ml) and streptomycin (250 ug/ml). Culture densities were adjusted to 5–10×10$^5$ cells/ml and media replenished twice a week.

The 5-78 T cell rabbit (AACR strain) lymphoma, and the EBV-infected B lymphoma B95-8 from marmosets were also maintained as suspension cultures. Their growth conditions were similar to that used for culture of the human lymphoma cell lines Human AMML, ALL and Hairy cell leukemia were obtained from untreated patients undergoing leukophoresis prior to chemotherapy. Leukemic cells were separated on Ficoll-Hypaque gradients and processed as outlined for L-1210 cells.

All cultures were incubated at 37° C. in a humidified atmosphere of 5% CO$_2$ in air. Media, culture fluids and cell suspension were routinely checked for bacterial and fungal contaminations by use of tryptose phosphate broth; cultures were also checked for mycoplasma contamination by the method of Todaro et al.

PREPARATION OF THE CHEMOTHERAPEUTIC AGENT

The tripeptide compound 3-(p-fluorophenyl)-L-alanyl-3-[m-bis(2-chloroethyl)aminophenyl]-L-alanyl-L-methionine ethyl ester hydrochloride) was initially dissolved at a concentration of 10 mg per ml of a solution of 0.25 ml of N,N-dimethylacetamide, 0.25 ml of absolute ethanol and 0.5 ml of propylene glycol. In the solvent solution, the absolute ethanol can be replaced with Tween 80 or other physiological and pharmaceutical emulsifiers. Stock solutions of one or two mg per ml were prepared by further dilution in an aqueous solution of 50% propylene glycol just prior to use. Aliquots of all stock solutions were added directly to the culture media to obtain a final concentration of 0.1–50 ug/ml. Controlled cultures treated with diluent received the identical volume of stock solution without the chemotherapeutic agent.

For treatment of B-type retrovirus the tripeptide, p-fluoro-L-phenylalanyl-m-bis-(2-chloroethyl)amino-L-phenyl-alanyl-methionine ethylester hydrochloride, was dissolved at 15 mM in N,N dimethyl acetamide, absolute ethanol, and propylene glycol (1:1:2). Stock solutions of the drug were directly diluted in the treatment medium consisting of RPMI-1640 with 10 uM insulin, 13.8 uM hydrocortisone, 2.5% FBS, and antibiotics.

TREATMENT OF MJY-ALPHA AND B-16 CELL LAYERS

MJY-alpha mammary tumor cell layers were initiated at 2×10$^5$ cells/2 cm$^2$ well (Nuncion Multidish 4, Vangard International, Neptune, NJ) using cells spontaneously released into the medium from confluent 6-8 day old cell layers. B-16 melanoma cells obtained from 4-day-old cell confluent cultures by trypsinization with STV were plated at 2.2×10$^5$ cells/cm$^2$ well. These seeding densities yielded lightly confluent layers (2.3–2.6×10$^5$ cell/cm$^2$). following treatment the layers were rinsed twice and reincubated with growth media:

media were changed daily until the cultures were terminated.

TREATMENT OF LYMPHOID CELL LINES AND HUMAN LEUKEMIAS

All rabbit, marmoset and human lymphoid in vitro cell lines, murine L-1210 leukemia and primary human leukemias were treated at cell concentrations of $6-10 \times 10^5$ cells/ml. The tripeptide was added to the cell suspensions to yield final concentrations of 1 to 50 ug/ml. Cultures were treated at 37° C. for periods ranging between 15 min to 24 hr. Following treatment, aliquots were removed and centrifuged at 800 rpm for 9 min, at 5° C. Treatment media were gently aspirated and the lymphoid cells resuspended in fresh growth media and reincubated at 37° C. Culture media were changed daily by gently pelleting the cells and exchanging 60–70% of the spent supernatant with fresh media.

TUMOR CELL SURVIVAL

Survival of tumor cell layers or suspensions was ascertained using 0.5% trypan blue in 0.1M phosphate-buffered saline, pH 7.25. Cell layers were released from the Multidish-4 wells with 0.5 ml STV, diluted 2 to 10 fold with the vital strain; tumor cells in suspension cultures were directly mixed 1:1 with the trypan blue dye. Tumor cells were enumerated using a haemocytometer; all 10 fields were counted for every sample. Percent viable cells was determined by direct comparison of the numbers of cells excluding trypan blue in treated cultures to those in untreated or diluent-treated parallel cultures. There were no significant differences in the viability of cells treated with diluent when compared to untreated cells.

TREATMENT OF B-TYPE RETROVIRUS

The tripeptide compound, PTT.119, is able to significantly reduce MMTV production in cells, such as MJY-alpha cells, either during continuous treatment or after a brief pulse exposure. Decreases in extracellular MMTV are dose related and continue one week following tripeptide treatment.

The mechanism(s) of PTT.119-induced depression of MMTV production is unknown. The general cytolytic activity of the tripeptide probably accounts for some of the inhibition, but it is unlikely that this is the sole cause of the decline in MMTV production. Reductions in viral replication are significantly greater than that accounted for by the cytolytic action of the tripeptide. MMTV production by mammary tumor cells treated with sublethal levels of PTT.119 (0.15 and 1.5 uM) is also affected. In addition, synthesis of intracellular viral proteins are unaffected at a PTT.119 dose inhibitory to MMTV production.

Various stages in the replicative cycle of retroviruses are proposed as possible sites for exogenous intervention. One of the common sites of inhibition of retrovirus replication shown to cause the inactivation of viral RNA-directed DNA polymerase. This inactivation prevents formation of the integrated DNA provirus. It is possible that PTT.119 inhibits this viral enzyme. However, this effect probably is not of consequence to a chronically infected cell such as the MJY-alpha since it already contains multiple integrated copies of the MMTV genome.

One of the primary reactions of the bis-(2-chloroethyl) amino component of PTT.119 is alkylation of guanine residues which can result in DNA miscoding, excision of altered residues, and possible crosslinking of two nucleic acid chains or nucleic acids to proteins. Alkylation of the proviral MMTV DNA can possibly inhibit transcription of structural and enzymatic virion proteins. Also, PTT.119 possibly interferes with glucocorticoid-modulated induction of MMTV transcription. Steriods bind with specific cellular receptors which then undergo activation and accumulation in the nucleus. These complexed glucocorticoid hormones recognize and bind to specific DNA sequences, thereby, inducing increased transcription levels. There are at least two such sites in the LTR region of integrated MMTV genomes. The addition of hydrocortisone to MMTV producing cells results in steriod-modulated induction of MMTV mRNA. Comparison of Tables 6 and 8 indicates that in the MJY-alpha cells this induction results in a two to three fold increase in MMTV protein and virion synthesis. PTT.119 can possibly specifically interfere with this hydrocortisone-modulated amplification of viral mRNA resulting in reduced levels of MMTV particles. However, quantitation of the levels and rates of synthesis of intracellular MMTV polyprotein precursors and cleavage products do not reveal any reduction in de novo synthesis. In contrast, the levels of all MMTV proteins in PTT.119-treated cells are elevated compared to untreated control cells. There is also no apparent alterations in the relative levels of the env and gag/pol polyprotein precursors and cleavage products in the tripeptide-treated cells. These results indicate that PTT.119 does not selectively alter or inhibit transcription or translation of structural MMTV proteins. The activity of PTT.119, which inhibits retrovirus replication, appears to be from the inactivation of the viral RNA-directed polymerase.

The paradox of increased intracellular levels of MMTV proteins and the concomitant reduction in extracellular virus production strongly indicates that the tripeptide interfers with either a late step in the processing and assembly of proteins and RNA, or in the release of viral particles. Ultrastructural examination of the PTT.119 treated cells does not reveal any accumulations of partial or completely formed particles. This indicates that virus release is not inhibited. If PTT.119 did inhibit replication of virion RNA or altered the genomic material, formation of the viral nucleoprotein core could be affected. The PTT.119-induced alterations in the levels of the major structural protein of the core is possibly a reflection of this interference. However, the reduction in viral p24 could also be the result of the direct interaction between the tripeptide and the processing of p24. The relationship of these structural changes to the inhibitory effects of PTT.119 on MMTV production has not yet been determined. It is not known if all MMTV particles from PTT.119-treated cells have equally reduced levels of the protein or if the virion population is comprised of several types of particles with varying amounts of p24.

The possible multifocal action of this antitumor tripeptide was a concern during examination of this compound. Since virus particles obtained by induction are infectious and oncogenic, PTT.119-treated cells were monitored for the presence of C-type virus. Induction of C-type virus in the MJY-alpha cells is possible since these mammary tumor cells have been shown to carry and express endogenous genomes. There was no detection of any endogenous virus production by the cells either following from a 0.5 to 48 hour pulse PTT.119 treatment or after culturing the cells in the tripeptide for 8 months. In addition, no diminution of the inhibitory effect of PTT.119 or enhancement of B-type retrovirus production was observed under these conditions. These results indicate that PTT.119 is probably not a potent retrovirus inducer.

The ability of PTT.119 to inhibit MMTV production and to alter the composition of the retrovirus being produced by chronically infected and transformed cells is believed to be unique. This antiviral activity of the tripeptide can enhance its therapeutic efficacy as an antitumor agent by reducing the possible retrovirus-induced reinduction of neoplasia in hosts. This characteristic of the tripeptide can be of great importance in light of the increasing frequency of detection of human retroviruses and their proviral DNA in human tumors and in the cells from patients with the highly fatal acquired immune deficiency syndrome (AIDS). The inhibition of MMTV by PTT.119 and the inability of the tripeptide to induce the expression of existing endogenous retrovirus enhances its suitability as a potential anticancer agent in man.

EXPERIMENTAL EXAMPLE 1

The ability of the tripeptide compound to inhibit the growth and survival of neoplastic cells was first assessed using the MJY-alpha mammary tumor cell line and the transplantable L-1210 leukemia. The numbers of viable cells in in vitro MJY-alpha cell layers and L-1210 cell suspensions were determined following continuous 24 hr. exposure to 0.1 to 50 ug of the tripeptide compound per ml. Significant decreases in mammary tumor (46-80%) and leukemia cells (18-94%) survival were observed at all concentrations of the tripeptide compound tested including dosages less than 10 ug/ml (Table 1). The results reveal that the cancericidal activity of the tripeptide compound resulted from the direct interaction of the drug with the tumor cells and that it did not require metabolic conversion by the animal hosts for activation.

TABLE 1

CYTOTOXIC EFFICACY OF THE TRIPEPTIDE COMPOUND AND PARENTAL COMPONENTS
L-1210 leukemia cell suspensions (1 × 10$^6$ cells/ml) and MJY-alpha mammary tumor cell layers (2.5 × 10$^5$ cells/cm$^2$) were treated for 24 hr and the percentage of viable cells compared to untreated cells and control cells receiving diluent.

Percent Tumor Cell Survival

| L-1210 Leukemia ug of Tripeptide compound/ml | | | | | MJY-Alpha Mammary Tumor ug of Tripeptide compound/ml | | | | |
|---|---|---|---|---|---|---|---|---|---|
| 0.1 | 1 | 5 | 10 | 25 | 1 | 5 | 10 | 25 | 50 |
| 82 | 70 | 62 | 28 | 6 | 54 | 41 | 36 | 27 | 20 |

EXPERIMENTAL EXAMPLE 2

In order to establish the in vitro spectrum of the cancericidal activity of the tripeptide compound against various cell types, leukemias of B and T cell origins, melanoma and mammary tumor cell lines were subjected to continuous tripeptide compound treatment. Loss of cellular viability was observed in all tumor cell lines following 24 hr exposure to the tripeptide compound (Table 2). Decreases in tumor cell survival were observed at all doses, and the sensitivity of each tumor cell line was dose dependent between the concentrations of 1 to 50 ug of tripeptide compound/ml. Comparison of the leukemia, melanoma, and mammary cancer cell types revealed that they were differentially susceptible to the tripeptide compound induced cytotoxicity at any given concentration of the tripeptide compound. Leukemia cells were usually more susceptible to the cancericidal action of the tripeptide compound and cellular toxicity was observed within the first 4 hrs of exposure. However, appreciable decreases in mammary tumor and melanoma cell survivals were detected only after 8 hrs of treatment with the tripeptide compound.

The tripeptide treatment of the murine mammary tumor cell lines, MJY-alpha, not only reduced tumor cell survival in a dose-dependent manner but also decreased the production of extra cellular mouse mammary tumor virus (MMTV). Replication of this B-type retrovirus was reduced by 27% when MJY-alpha cells were exposed to 10 microgram of the tripeptide/ml for zero to 24 hours; continuous treatment for another 24 hours further reduced MMTV production by 82%. These decreases could not be accounted for by the degree of the tripeptide induced sytolysis; tumor cell survival was reduced by only 8% and 25%, respectively, during these time periods.

In order to unravel the antimetabolic activity of the tripeptide, we carried out several experiments to ascertain the effects of the compound on viral replication. Our previously described studies assessing the cancericidal activity of the tripeptide in nine tumor cell lines (Table 2) indicated that in addition to the increased sensitivity of lymphoma-leukemia cells to the agent, cells infected with and producing RNA or DNA viruses were generally more sensitive. Examination of the cellular metabolism using radio-labeled nucleic and amino acids demonstrated that the antiviral activity was not the result of blockage in cellular uptake and incorporation of precursors.

Utilizing isotopically-labeled uridine, a significant decrease was detected in the production of the RNA tumor virus MMTV by the MJY-alpha mammary tumor cells. Viral replication was reduced by 42% when cells were treated with 10 ug of the tripeptide at the time of labeling. Cultures treated with this concentration 24 hours following radiolabeling of the cells also produced 37% less MMTV compared to controls, indicating that antiviral activity was not merely the result of a cellular blockage in the uptake of precursors.

The structural proteins on MMTV virions purified from cultures treated with the tripeptide were analyzed in order to determine if the tripeptide induced any biochemical changes in the particles. Profiles of MMTV glycol proteins and non-glycosylated polypeptides obtained by sodium dodecyl-sulfate polyacrylamide gel electrophoresis revealed a specific 60 to 78% decrease in the major non-glycosylated core protein, P24. The relative levels of the other MMTV polypeptides were not affected.

TABLE 2

Tumor cell layers and suspensions were exposed to 1 to 50 ug of the tripeptide salt per ml for 24 hr. Viability was determined after 1, 4, 8 and 24 hr. of treatment. Results are the average of duplicate samples of at least three separate experiments.

| Cell Line | Cell Type | Virus Type | Pro-duction | Tri-peptide ug/ml | % tumor cell survival exposure (hr) | | | |
|---|---|---|---|---|---|---|---|---|
| | | | | | 1 | 4 | 8 | 24 |
| Mouse | | | | | | | | |
| L-1210 | Leukemia | MuLV | + | 1 | 95 | ND | 100 | 65 |
| | | | | 5 | 100 | 84 | ND | 57 |
| | | | | 10 | 92 | 75 | ND | 12 |
| | | | | 25 | 50 | 25 | 15 | 0 |
| B-16 | Melanoma | — | — | 5 | 100 | 100 | 100 | 74 |
| | | | | 10 | 100 | 100 | 63 | 64 |
| | | | | 25 | 100 | 100 | 92 | 60 |
| | | | | 50 | 100 | 100 | 58 | 33 |
| MJY-alpha | Mammary Tumor | MMTV | ++ | 5 | 100 | 100 | 100 | 53 |
| | | | | 10 | 100 | 100 | 100 | 53 |
| | | | | 25 | 100 | 100 | 98 | 25 |
| | | | | 50 | 98 | 87 | 62 | 19 |
| Rabbit | | | | | | | | |
| 5-78 | T-lymphoma | HVA | + | 5 | 100 | 88 | ND | 66 |
| | | | | 10 | 89 | 61 | ND | 49 |
| | | | | 25 | 75 | 32 | 14 | 6 |
| | | | | 50 | 57 | 4 | ND | 2 |
| Marmorset | | | | | | | | |
| B-95-8 | B-lymphoma | EBV | + | 10 | 100 | 100 | ND | 40 |
| | | | | 25 | 100 | 86 | 49 | 20 |
| | | | | 50 | 77 | 42 | 26 | 6 |
| Human | | | | | | | | |
| Raji | B-lymphoma | EBV | — | 10 | 98 | 98 | ND | 82 |
| | | | | 25 | 100 | 97 | 97 | 35 |
| | | | | 50 | 94 | 90 | 76 | 20 |
| P HR-1 | B-lymphoma | EBV | + | 10 | 96 | 91 | ND | 75 |
| | | | | 25 | 92 | 86 | ND | 69 |
| | | | | 50 | 93 | 75 | ND | 60 |

1. MuLV = murine leukemia virus; MMTV = mouse mammary tumor virus; HVA = herpes-virus ateles; EBV = Epstein-Barr virus.
2. ND = Not Done.

EXPERIMENTAL EXAMPLE 3

Leukemic cells obtained by leukophoresis from untreated patients with Hairy cell, AMML, and ALL leukemias were continuously treated with the tripeptide compound (Table 3). Lymphoblast from a patient with ALL leukemia were particularly sensitive to the tripeptide compound; cell survival was reduced by 75% following treatment with as low as 1 ug of the tripeptide compound, AMML and Hairy cell leukemias were also sensitive to all concentrations of the tripeptide compound; the numbers of viable cells were reduced by 34% to 96% after 24 hr treatment. It is noteworthy that cytotoxicity was detected in the fresh leukemia preparations within the first hour of the tripeptide compound treatment; the surviving fractions ranged from 0 to 100% in a dose dependent manner. Similar levels of cell death were never immediately observed in any of the tumor cell models at these concentrations. The cancericidal activity of the tripeptide compound was also greater against uncultured human tumor cells than any of the tumor cell lines after 24 hrs of treatment.

TABLE 3

EFFICACY OF THE TRIPEPTIDE SALT AGAINST HUMAN CELLS

Human leukemic cells obtained by leukophoresis from untreated patients were treated with 1 to 50 ug of the tripeptide salt for 24 hr. Tumor cell viability was determined on duplicate samples following 1, 4, and 24 hr. exposure.

| | Concentration Tripeptide (ug/ml) | % Tumor cell survival Exposure (hr) | | |
|---|---|---|---|---|
| | | 1 | 4 | 24 |
| Hairy cell leukemia | 5 | 100 | 80 | 34 |
| | 10 | 100 | 71 | 81 |
| | 25 | 92 | 71 | 12 |
| | 50 | 37 | 21 | 7 |
| AMML | 1 | 95 | 85 | 66 |
| | 5 | 50 | 52 | 6 |
| | 10 | 60 | 41 | 21 |
| | 25 | 20 | 15 | 14 |
| | 50 | 4 | 3 | 4 |
| ALL (N cell leukemia) | 1 | 98 | 76 | 25 |
| | 5 | 46 | 29 | 7 |
| | 10 | 32 | 15 | 0 |
| | 25 | 15 | 15 | 0 |
| | 50 | 0 | 0 | 0 |

EXPERIMENTAL EXAMPLE 4

Several of the tumor cell models and the primary human leukemias displayed tripeptide compound induced cytotoxicity within 1 to 4 hours of exposure to the tripeptide compound indicating that continuous 24 hr treatment may not be required for the reduction of the tumor cell populations. To delineate the minimum concentration and duration of the tripeptide compound exposure to induce cytolysis, MJY-alpha and B-16 melanoma cell layers and L-1210 leukemia cell suspensions were exposed to 0.5 to 50 ug of the tripeptide compound per ml of solvent for 0.25 to 4 hours. The tripeptide compound was then removed and the cells washed and reincubated in media growth. Tumor cell viability was determined 24 hrs after pulse tripeptide compound exposure. Cell survival of all three tumor cell lines was reduced by an exposure period of as short as 15 min (Table 4). The degree of cytolysis increased with extension of the treatment periods from 15 min to 4 hrs, although the decreases in cell survival were not proportional to the duration of the exposure. However, a concentration dependent decrease in cell survival was observed in the three murine tumor models for each treatment period. Comparison of the data in Tables 2 and 4 reveal that cells exposed to the tripeptide compound for one hour were irreversibly damaged when assayed a day later despite their apparent viability immediately after treatment. Of greater importance was the demonstration that pulse exposure to any concentration of the tripeptide compound was almost as effective as continuous 24 hr treatment in reducing the number of tumor cells.

TABLE 4

SUSCEPTIBILITY OF TUMOR CELLS TO PULSE-TREATMENT WITH THE TRIPEPTIDE SALT
MJY-alpha mammary tumor and B-16 melanoma cell layers and L-1210 leukemia cell suspensions were pulse-treated with the tripeptide salt, washed with media and their viability determined 24 hr. later. Values are the average of duplicate samples from four experiments.

| | | Percent Tumor Cell Survival Treatment Period (hr) | | | | |
|---|---|---|---|---|---|---|
| Cell Line | Tripeptide | .25 | .5 | 1 | 2 | 4 |
| MJY-alpha | 5 | ND[1] | 94 | 89 | 77 | 76 |
| | 10 | 68 | 67 | 70 | 64 | 48 |
| | 25 | 61 | 37 | 51 | 46 | 44 |
| | 50 | 45 | 32 | 41 | ND | ND |
| B-16 Melanoma | 5 | ND | 93 | 88 | 66 | 79 |
| | 10 | ND | 75 | 68 | 73 | 63 |
| | 25 | 82 | 67 | 60 | 56 | 52 |
| | 50 | 65 | 62 | 48 | ND | ND |
| L-1210 Leukemia | .5 | 95 | 90 | 83 | 94 | 68 |
| | 1 | 80 | 87 | 83 | 78 | 45 |
| | 5 | 72 | 60 | 61 | 57 | 35 |
| | 10 | 53 | 40 | 27 | 31 | 37 |
| | 25 | 20 | 7 | 0 | 0 | 0 |
| | 20 | 0 | 0 | 0 | ND | ND |

[1]ND = Not Done.

EXPERIMENTAL EXAMPLE 5

Figure 2:
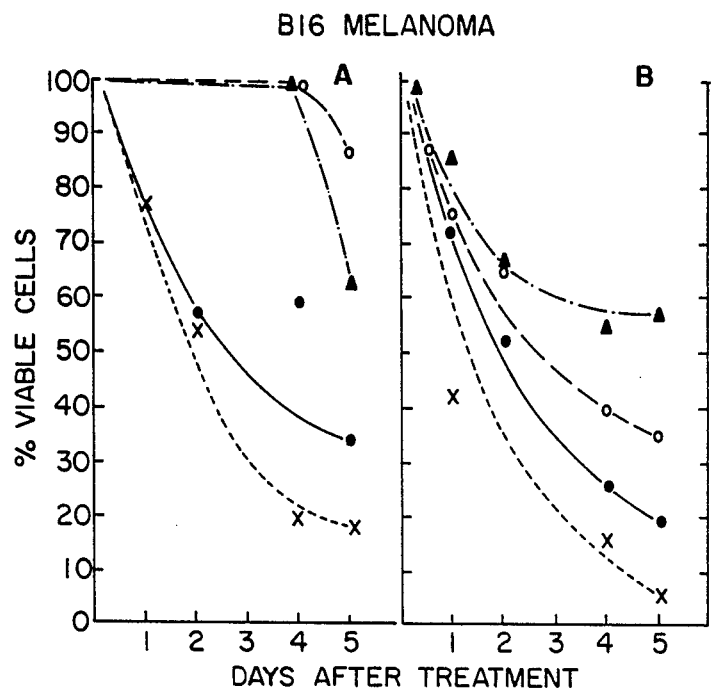
FIG. 2 shows survival of B-16 melanoma cell layers following 30 min (A) or 1 hr (B) pulse treatment with 5 (▲-..-▲), 10 (o - - o), 25 (●-●), and 50 (X - - X) ug of the tripeptide ml of carrier solvent. The numbers of cells in the 24-hr-old layers at the time of treatment were $2.7-3\times10^5$ B-16 melanoma cells per well. The ranges of viable control cell numbers during the 5-day observation period were $3.5-12\times10^5$ MJY-alpha cells and $1.5-4\times10^5$ B-16 cells per well.
Figure 3:
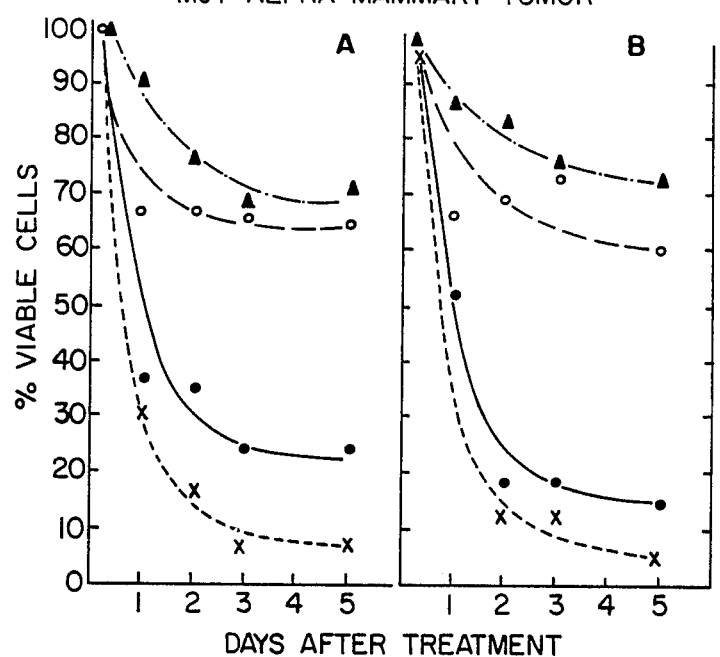
FIG. 3 shows survival of MJY-alpha mammary tumor cells following 30 min (A) or 1 hr (B) pulse treatment with 5 (▲-..-▲), 10 (o - - o), 25 (●-●) and 50 (X - - X) ug of the tripeptide/ml of carrier solvent. The numbers of cells in the 24-hr-old layers at the time of treatment were $2.9-3.2\times10^5$ MJY-alpha cells. The ranges of viable control cell numbers during the 5-day observation period were $3.5-12\times10^5$ MJY-alpha cells.

Pulse treatment of mammary, melanoma and leukemia tumor cells with the tripeptide compound reduced the number of viable cells 24 hrs after exposure. In order to ascertain if the remaining cells were resistant to the tripeptide compound and be able to replicate and repopulate the culture vessels, longitudinal assessments of the surviving cell fractions were made. MJY-alpha mammary tumor and B-16 melanoma cell layers, and L-1210 leukemia cell suspensions were treated with 1 to 50 ug of the tripeptide compound per ml for 30 min or 1 hr. Cell viabilities were determined over 5 days (FIGS. 1-3). In all three tumor systems, cell viabilities decreased over the examination period indicating that the population was irreversibly affected by pulse exposure to tripeptide compound. The degrees and rates of tumor cell susceptibility were dependent on the tumor cell system, as well as, on the concentration and duration of the tripeptide compound exposure. Of the three tumor models, the L-1210 leukemia was the most susceptible; at any given concentration of the tripeptide compound, approximately 5 times more L-1210 cells were destroyed compared to mammary tumor and melanoma cells.

Unlike either the L-1210 leukemia and B-16 melanoma cultures which showed a gradual progression of cell cytotoxicity with increasing dosages, there was a distinct separation of cell viability between 10 and 25 ug/ml in MJY-alpha mammary tumor cells (FIG. 3). Whether this reflected a critical threshold level of the tripeptide compound for this cell line or demarcated two populations of susceptible cells is not known. In all three tumor systems, extension of the treatment period from 0.5 to 1 hour usually resulted in a more rapid rate of cell death during the first 2 to 3 days following exposure, but did not necessarily effect the total numbers of viable cells remaining on days 4 and 5. It is also significant that the cancericidal activity of the tripeptide compound was more pronounced against fresh, human ALL, AMML and Hairy cell leukemias than established tumor cell lines of murine, rabbit, primate and human origins.

IN VIVO PREPARATION

EXPERIMENTAL EXAMPLE 6

Figure 4:
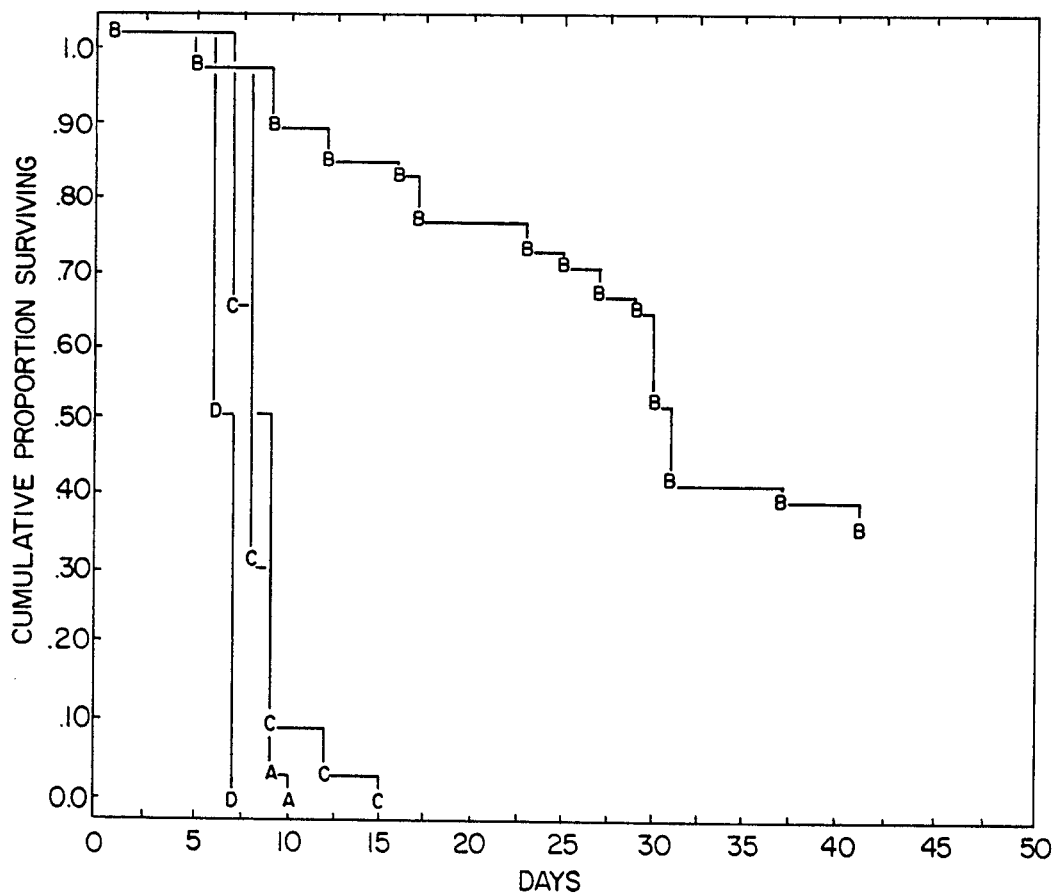
FIG. 4 shows DBA/2 mice inoculated intraperitoneally with $10^6$ L-1210 leukemia cells on Day 0. (A) Control animals. Mice were treated on Day 2 with the tripeptide at (B) 10 mg/kg of rodent weight; (C) 15 mg/kg; and (D) 20 mg/kg.

In view of the broad spectrum of in vitro therapeutic activity of the tripeptide compound against murine, rabbit, primate, and human tumor cell lines, an experiment was initiated to determine the in vivo therapeutic activity of the tripeptide compound. The following experiments were performed with the tripeptide compound. Male mice were inoculated intraperitoneally on day 0 with $10^6$ untreated leukemia L-1210 cells. The tumor bearing mice were treated 48 hours later with a single dose of 10, 15, and 20 mg of the tripeptide compound per kg weight of the test animal. Results clearly demonstrate the tripeptide compound effectively reduced the tumor burden with an increase of the mean survival time from 8 to 30 days (275%) and the apparent "cure" of the 30% of the treated animals. See FIG. 4.

EXPERIMENTAL EXAMPLE 7

Leukemia in AKR mice, which is the result of the oncogenic activity of the endogenous Gross leukemia virus, has been effectively used as a model for human leukemias in the studies of tumor biology, chemotherapy, and chemoimmunotherapy. There is considerable evidence that leukemia in the AKR mice mimics human leukemias in many respects, and it is probable that AKR leukemia is analogous to human acute T-cell lymphocytic leukemia. Leukemic cells first appear in the thymus of mice at 6 to 12 months of age. Controlling this disease is formidable, since the cure or long range control of spontaneous leukemia in AKR mice require the therapeutic eradication of virtually all of the oncogenic cells. The time lapse between the first appearance of viable lymphoma cells in the thymus and the clinical diagnosis is about 30 days.

Figure 5:
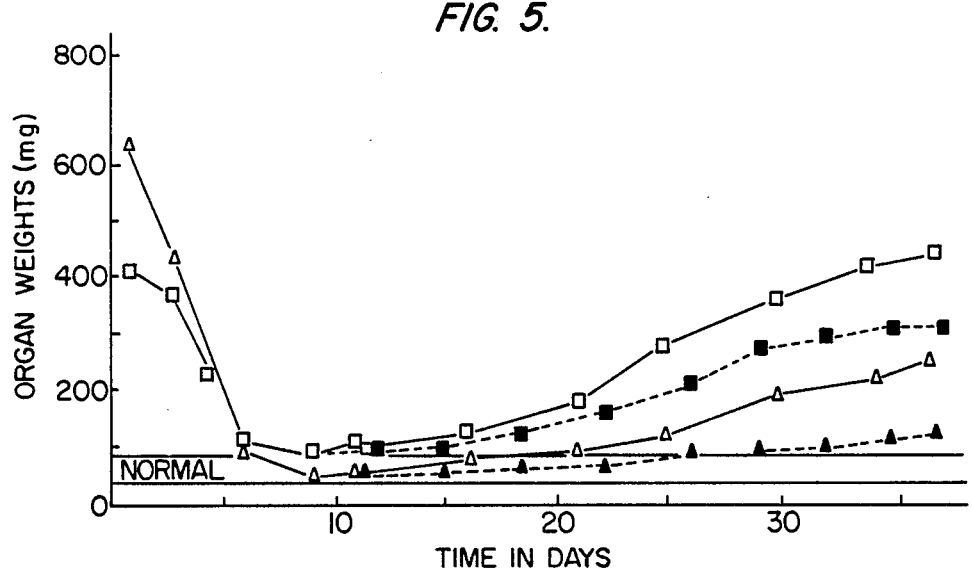
FIG. 5 shows change of organ weights after chemotherapy with the tripeptide treated AKR mice with spontaneous leukemia. Chemotherapy consisted of: Group A: 10 mg/kg of rodent weight on days 1 and 14; Group B: 5 mg/kg on days 1, 4, 7, 21, and 42. At designated intervals 4 mice from each experimental group were selected at random, sacrificed and their spleen and thymys weights determined. Group A: Mean thymus wt (Δ - - Δ); Mean splean wt (□ - - □) Group B: Mean thymus wt (▲- - ▲); Mean spleen wt (■- - ■).
Figure 6:
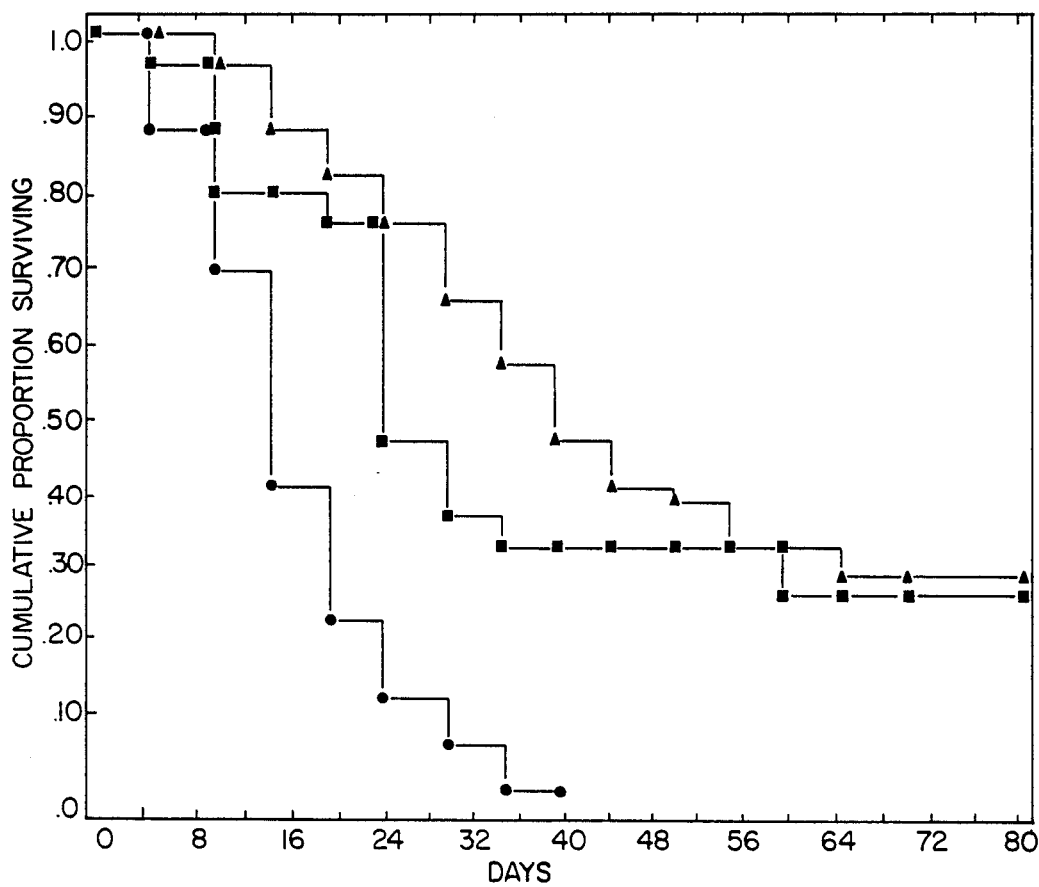
FIG. 6 shows AKR mice with spontaneous leukemia. Control mice (o); mice received intraperitoneal injections of the tripeptide at 10 mg/kg on days 1 and 14 (Therapy A; ■), and 5 mg/kg on days 1, 4, 6, 21, and 42 (Therapy B; ▲).

The effectiveness of the tripeptide compound in the treatment of spontaneous leukemia in AKR mice was tested. The clinical diagnosis of spontaneous leukemia in AKR mice was made with 95% accuracy by splenic and lymph node palpation, followed by leukocyte count. There is good evidence that at the time of clinical diagnosis there are $0.6-1.8 \times 10^9$ widely disseminated lymphoma cells in AKR mice. Without cytoreductive therapy, AKR mice die after diagnosis of spontaneous leukemia at the rate of 50% by 14 days, 90% by 33 days, and 96% by 56 days. In the preliminary experiment using AKR mice with spontaneous leukemia, good remission induction was achieved with the tripeptide compound administered either at 10 mg per kg weight of test animal on days 1 and 14, or at 5 mg of the tripeptide compound per kg of the test animal on days 1, 4, 7, 21, and 42. Significant reductions in leukemic thymus and spleen weights were observed after chemotherapy (FIG. 5). Reduction of thymus and spleen weights to normal is indicative of eradication of the primary tumor. Leukemic AKR mice receiving either treatment sustained a mean survival time of 200% and 100%, respectively. It is also important and significant that the tripeptide compound treatment provides good sustainment since 30% of the treated animals in either group were alive after the onset on the therapy (FIG. 6).

EXPERIMENTAL EXAMPLE 8

Figure 7:
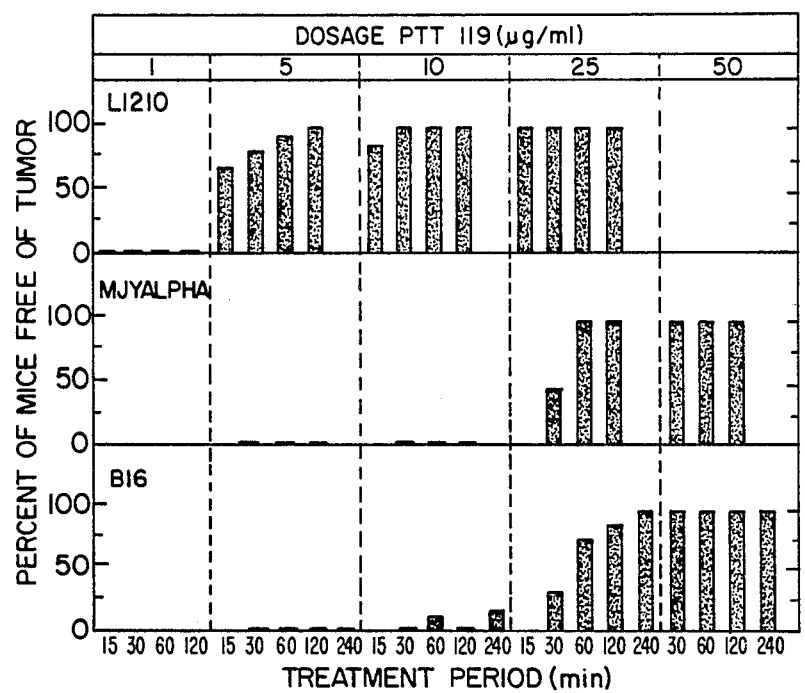
FIG. 7 shows in vivo tumorigenicity of L-1210 leukemia, MJY-alpha mammary tumor, and B-16 melanoma treated with 1 to 50 ug of the tripeptide/ml. Tumor cells were treated for 15 min to 4 hr, washed and grafted into syngeneic hosts at a concentration of $1\times10^6$.

Data presented in FIG. 7 shows that L-1210 leukemia cells were the most susceptible to the cancericidal activity of the tripeptide. Concentrations as low as 5 and 10 ug tripeptide/ml effectively abrogated the leukemogenicity of the L-1210 cells. No tumor growth was apparent in the recipient mice receiving L-1210 cells treated with 5 ug for 2 hr, or 10 ug for 30 min or longer. The synthetic tripeptide effectively reduced the population of L-1210 cells capable of proliferation to 0. To ascertain if the recipitients' immune responses were elicited against the tripeptide-treated leukemia cells, $BDf_1$ mice which had survived unsuccessful grafts of tripeptide-treated L-1210 leukemia cells for 45 days were challenged with a second graft of 1000 untreated L-1210 cells. There were no differences in the leukemogenesis of the L-1210 cells in these recipients and all mice like the controls died of tumor on days 12 and 13 demonstrating that implantation of L-1210 cells treated with tripeptide did not confer protection on the hosts to future grafts.

Loss of tumorigenicity of MJY-alpha mammary tumor and B-16 melanoma tumor cells was also apparent following tripeptide treatment (FIG. 7). In both tumor systems complete absence of tumor growth was observed in recipients of $10^6$ cells treated with tripeptide concentration of 25 ug or higher for 30 to 240 min. Exposure to the tripeptide compound reduced the viable population of MJY-alpha and B-16 tumor cells by at least 99.9% since their $LD_{100}$ doses are 100 viable cells. At lower tripeptide dosages, complete elimination of L-1210 leukemia, MJY-alpha mammary tumor and B-16 melanoma tumorigenicity were unattainable and significant extensions of the mean survival time (MST) of the recipient mice were observed (Table 5). $BDf_1$ mice receiving L-1210 leukemia cells treated with 5 ug of the tripeptide compound for 30 or 60 min had an ILS (increased life span) of 110% and 220%, respectively. Similarly, the survival of BALB/c mice implanted with $10^6$ MJY-alpha mammary tumor cells or C57BL/6 mice receiving B-16 melanoma cells treated with 5 to 25 ug tripeptide/ml were extended significantly beyond the 42 or 28 days, respectively, observed in the control hosts.

TABLE 5

MEAN SURVIVAL TIME (MST) OF SYNGENEIC RECIPIENTS OF TRIPEPTIDE TREATED TUMOR CELLS

Tumor cells were treated with the tripeptide compound in vitro, washed and implanted subcultaneously into syngeneic hosts as described in materials and methods. Numbers of surviving animals were quantitated every two days. All values represent the average of two experiments each containing groups of 10–15 mice.

| Tumor Cell | Tripeptide (ug/ml) | Treatment Period (min) | | | | |
|---|---|---|---|---|---|---|
| | | 15 | 30 | 60 | 120 | 240 |
| L-1210 Leukemia | 0 | 10 | 10 | 10 | 10 | — |
| | 1 | 10 | 10 | 11 | 13 | — |
| | 5 | 13 | 21* | 32* | NT[1] | — |
| | 10 | 8 | NT | NT | NT | — |
| | 25 | NT | NT | NT | NT | — |
| MJY-alpha Mammary Tumor | 0 | — | 42 | 42 | 42 | — |
| | 5 | — | — | 52* | 43 | — |
| | 10 | — | 44 | 46 | 61* | — |
| | 25 | — | 56* | NT | NT | — |
| | 50 | — | NT | NT | NT | — |
| B-16 Melanoma | 0 | — | 28 | 28 | 28 | 28 |
| | 5 | — | — | 31 | 33* | 41* |
| | 10 | — | 35* | 35* | 35* | 45* |
| | 25 | — | 52* | 68* | 65* | NT |
| | 50 | — | NT | NT | NT | NT |

[1]NT = No Tumor.
*p 0.001

EXPERIMENTAL EXAMPLE 9

BIOASSAY OF TUMORIGENICITY

Suspensions of untreated and tripeptide treated MJY-alpha mammary tumor, B-16 melanoma, and L-1210 leukemia cells were adjusted to a concentration of $1 \times 10^7$ cells/ml based on the initial tumor cell concentration before the tripeptide exposure. Tumor cells were inoculated into syngeneic hosts at a concentration of $1 \times 10^6$ cells in 0.1 l ml. Female BALB/c/Crgl recipients of MJY-alpha mammary tumor cells and male C57BL/6/Jx hosts receiving B16 melanoma cells were inoculated subcutaneously; $BDf_1$ mice were given intraperitoneal injections of L-1210 cells. Subcutaneous tumors were measured along their long and short axes every 1 to 3 days; tumor size is reported as the product of the two measurements ($mm^2$). See FIG. 8. The examination periods for mice receiving L-1210, MJY-alpha and B-16 tumor grafts were 45, 80, and 85 days, respectively. All mice were autopsied at the time of death or sacrifice.

Figure 8:
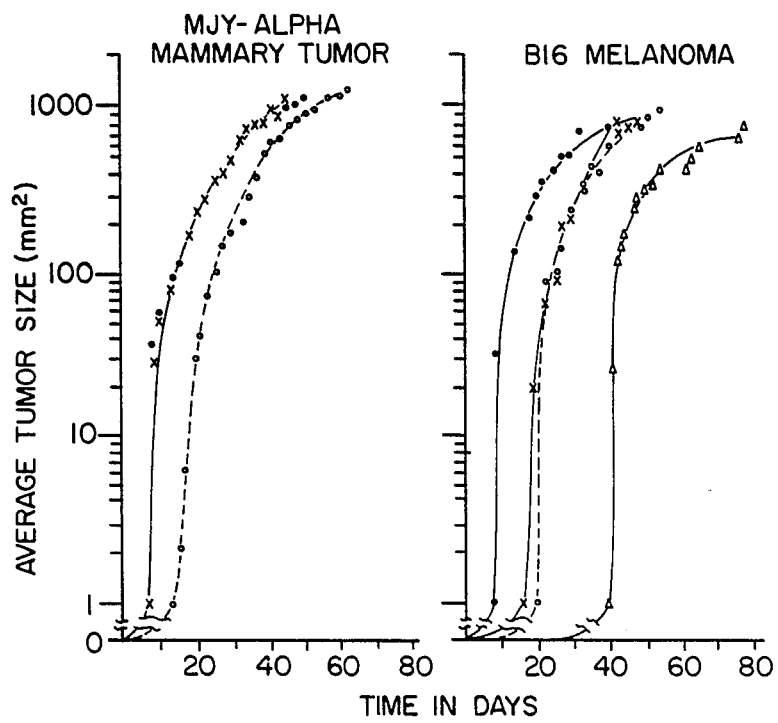
FIG. 8 shows average tumor size of MJY-alpha mammary tumor cells or B-16 melanoma implanted into BALB/c and C57BL/6 mice, respectively as a function of time after implantation. Tumor cells were treated for 2 hrs with 0 (o—o), 5 (x—x), 10 (o—o), 25 (Δ-Δ), and 50 (□—□) ug of tripeptide/ml, washed and grafted at $10^6$ cells s.c. The readings are averages obtained from 2 experiments with a total of 25 to 40 animals per group.

Assessment of the tumor growth rates of the subcutaneously implanted MJY-alpha mammary tumor and B-16 melanoma cells revealed that the initial lag period between inoculation of tumor cells and the appearance of palpable tumors lengthened in both solid tumor model systems with increasing dosages of tripeptide (FIG. 8). However, tripeptide did not alter tumor progression once the graft was established; tumor growth rates of untreated and tripeptide treated MJY-alpha and B-16 cells were identical and the maximum size of the tumor at the time of death of hosts remained unchanged. This suggested that the tripeptide did not alter the kinetics of tumor cell proliferation nor did it appear to select one subpopulation of tumor cells.

EXPERIMENTAL EXAMPLE 10

SENSITIVITY OF MICE TO THE TRIPEPTIDE COMPOUND

In order to assess whether the effective cancericidal concentrations of the tripeptide compound found in the bioassays were attainable in vivo, mice were given a single intraperitoneal inoculation of the tripeptide. Demonstrable tripeptide toxicity required administration of high concentrations of the synthetic tripeptide. All mice tolerated doses of 52.5 mg/m$^2$ (15 mg/kg) with no observable signs of discomfort or pathologies. BDf$_1$ males which have been previously shown to be very sensitive to alkylating agents tolerated 61.25 mg PTT.119/m$^2$ (17.5 mg/kg; LD$_{10}$), whereas, this dose increased to 74.6 mg/m$^2$ (21.3 mg/kg) in AKR females. The LD$_{50}$ of male BDf$_1$ mice was 81.6 Mg/m$^2$ (23.3 mg/kg) and 93.5 mg/m$^2$ (27 mg/kg) for female AKR mice.

EXPERIMENTAL EXAMPLE 11

IN VITRO SURVIVAL OF TRIPEPTIDE-RLEATED TUMOR CELLS

Figure 9:
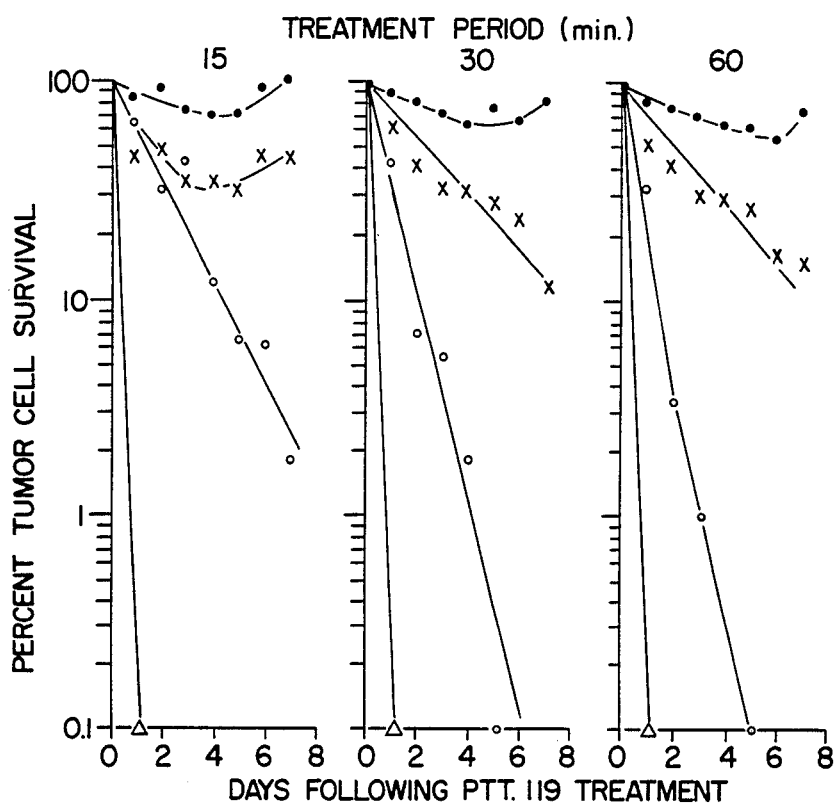
FIG. 9 shows survival of L-1210 leukemia cells following 5, 30 and 60 min treatment with 1 (●—●), 5 (x—x), 10 (o—o), 25 (Δ—Δ) uf of tripeptide/ml. L-1210 cell suspsensions contained $1\times10^6$ cells at the time of treatment. Viability was determined for 7 days and the data represent the average of duplicate samples from 2 experiments.
Figure 10:
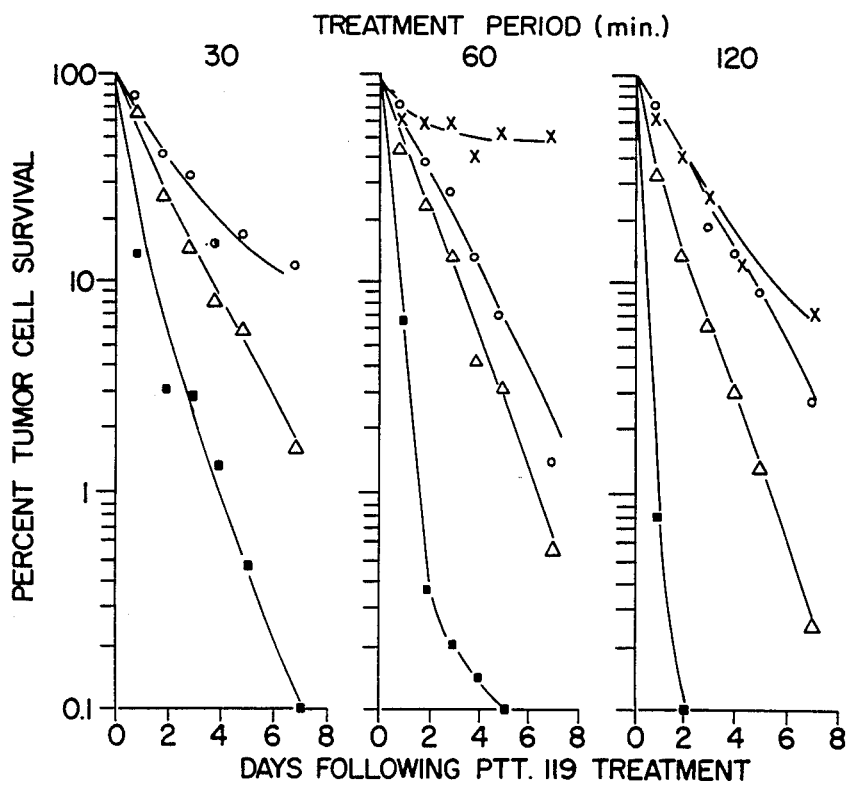
FIG. 10 shows survival of MJY-alpha mammary tumor cells following 30, 60 and 120 min exposure to the tripeptide concentrations of 5 (x—x), 10 (o—o), 25 (Δ—Δ), and 50 (■— ■) ug/ml (5 ug/ml at 30 minutes not shown). Cells were treated at $1\times10^6$ cells/ml and were then seeded at $2\times10^5$ cells/2 2 cm$^2$ following washing. Viability was monitored daily for 7 days. The data represent the average of duplicate samples from 3 experiments.
Figure 11:
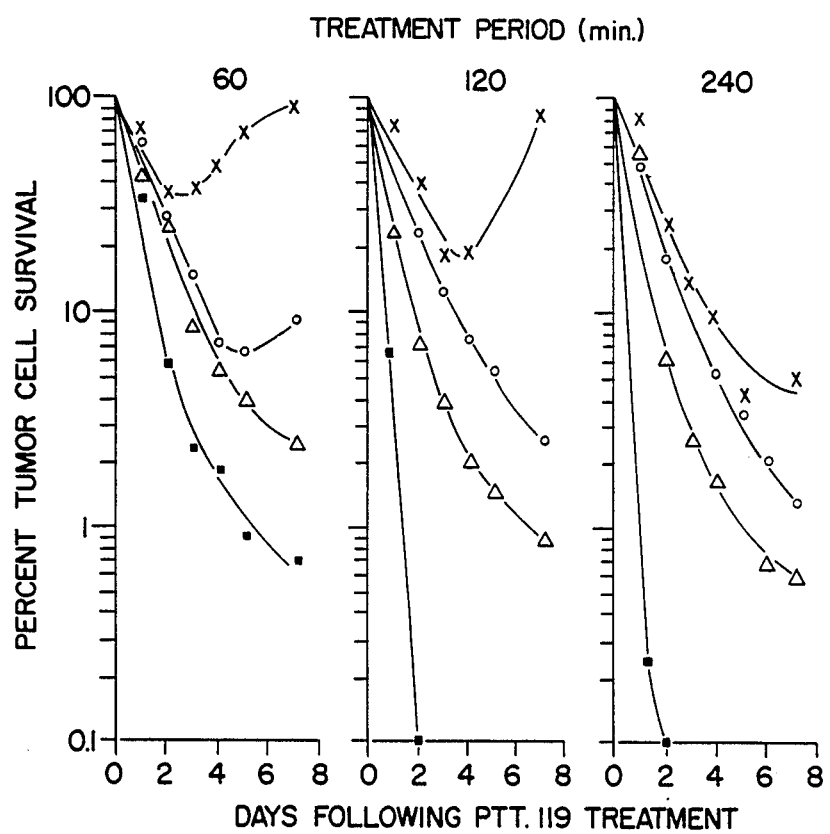
FIG. 11 shows survival of B-16 melanoma cells following 60, 120 and 240 min exposure to 5 (x—x), 10 o—o), 25 (Δ—Δ), and 50 (■— ■) ug of tripeptide/ml. B-16 cells were treated at a concentration of $6\times10^5$, washed, seeded at $2.2\times10^5$ cells/2 cm$^2$ and viability determined for 7 days. Data represent the average of duplicate samples from 3 experiments.

The reversibility of the cancericidal activity of the tripeptide compounds on L-1210 leukemia, MJY-alpha mammary tumor and B-16 melanoma cells was also monitored in the nonhostile tissue culture environment. Cell suspensions of these tumor models were treated with tripeptide for 15 to 240 min, washed and either inoculated into mice or maintained as suspension (L-1210) or monolayer cultures (MJY-alpha and B-16). Reductions in tumor cells survival were negligible (0-6%) in all three tumor systems at initiation of in vitro cultures following treatment with 50 ug tripeptide/ml for as long as 4 hrs. However, significant decreases in cellular viabilities of L-1210 leukemia (FIG. 9), MJY-alpha mammary tumor (FIG. 10) and B-16 melanoma (FIG. 11) tumor cells were observed 24 hr following tripeptide exposure and for the next 6 days.

Longitudinal examination of the cultures demonstrated that cytolysis of the tumor cells continued days after tripeptide treatment and also revealed the repopulation of tumor cell cultures treated with low concentrations of the tripeptide. A step-wise gradation in cytolysis with increasing concentrations of tripeptide was observed in the in vitro survival curves of the three tumor cell systems. At any dose of tripeptide, tumor cell survival also decreased when the treatment periods were lengthened although the L-1210, MJY-alpha and B-16 cells were refractile to these duration-related changes at several concentrations of the tripeptide. These apparent refractory phases were observed at concentrations of 10 and 25 ug of tripeptide in MJY-alpha and B-16 cells and at 1 and 5 ug of tripeptide in L-1210 leukemia cultures.

EXPERIMENTAL EXAMPLE 12

Figure 12:
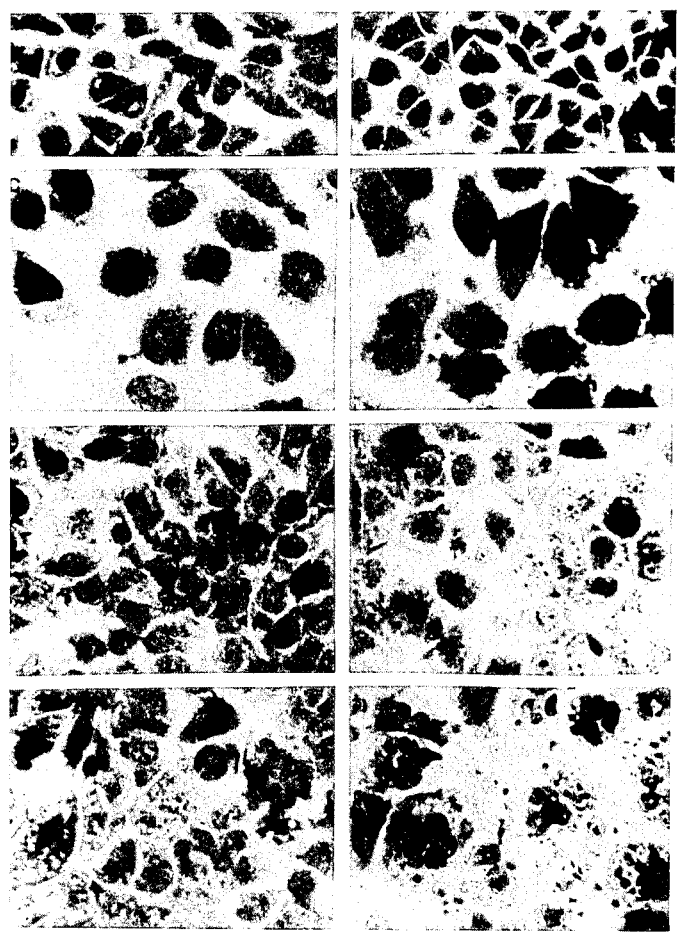
FIG. 12 shows the result of eight (8) different treatments of MJY-alpha mammary tumor cell layers after incubation. The photomicrographs were at 340 powers of magnification, except for photographs c and d which were at 670 powers of magnification. The tumor cells were treated as follows: a. With diluent only for 60 minutes, incubated one (1) day; b. With diluent only for 60 minutes, incubated four (4) days; c. With 25 ug PTT.119 for 15 minutes, no incubation—immediately after exposure; d. With 25 ug PTT.119 for 60 minutes, no incubation—immediately after exposure; e. With 10 ug PTT.119 for 60 minutes, one (1) day incubation; f. With 10 ug PTT.119 for 60 minutes, two (2) days incubation; g. With 10 ug PTT.119 for 60 minutes, four (4) days incubation; h. With 10 ug PTT.119 for 60 minutes seven (7) days incubation.

Confluent MJY-alpha mammery tumor cell layers were treated with PTT.199 or diluent for 15 or 60 minutes, washed, and then incubated in growth medium. Representative cell layers were fixed and stained with May-Grunwald-Giemsa stain from one (1) to seven (7) days after treatment as specified. Hemicysts or domes which are usually observed in short-term cultures of murine, MMTV-induced mammary tumors are not present in MJY-alpha cultures (FIG. 12a and b). Cell layers treated with 5 and 10 ug PTT.119/ml for 15 to 60 minutes appeared unchanged. Cellular pseudopodia were withdrawn and the cytoplasm appeared condensed around the nuclei (FIG. 12c and d). The most striking feature of exposure to high concentrations of PTT.119 was the ruffling of the plasma membrane and the formation of vesicles and blebs. The first detectable change was hypertrophy of the cells which initially appeared to be primarily due to increases in nuclear size as seen by comparison of FIGS. 12a and 12c. This alteration was closely followed by visible increases in the cytosol volume or rarefaction of the cytoplasm (FIG. 12f). The degree of further pathological alterations of MJY-alpha mammary tumor cells was dependent on the dosage of PTT.119 and included lobulation and fragmentation of the nuclei, and the formation of multinuclear cells (FIG. 12f and h). The increasing presence of multinucleated cells and the decreasing numbers of viable cells in these cultures indicated that cell division was not completed. Chromosomal condensation was not inhibited in multinucleated cells or in cells with highly lobulated or fragmented nuclei (FIG. 12h). FIG. 12g shows the same degree of increasing cell problem of induced irreversible nuclear fragmentation and lobulation, multi nucleation mitotic asynchrony.

EXPERIMENTAL EXAMPLE 13

Figure 13:
FIG. 13 shows four (4) thin sections of MJY-alpha mammary tumor cells with magnification at 45,000X through an electron microscope. Photograph A shows budding and mature B-type virus particles both in the main photograph and in the insert, for untreated cells. Photograph B shows untreated cells with aggregates of intracytoplasmic A-type virus particles and also numerous microvilli with budding particles. Photograph C shows cells treated with 25 ug PTT.119/ml for 2 hours, washed, and then incubated for one (1) day before processing for electron microscopy. Although there are some microvilli with budding particles present, the number is reduced from Photographs A and B. Photograph D shows cells treated and washed in the same way as in C, but allowed to incubate 2 days before being porcessed for electron microscopy. The number of microvilli to be observed are decreased from the number in Photographs A and B.
Figure 13:
Figure 13:
Figure 13:

Thin sections MJY-alpha mammary tumor cells were prepared according to standard techniques for electronmicroscopy. The magnification was scaled where the bar was equal to one um. As seen in part a, the untreated cells contain budding and mature B-type mouse mammary tumor virus particles. The tumor virus particles are shown in the insert and also throughout the lower two-thirds of the photograph as rope-like sections. Section B of FIG. 13 shows untreated cells containing aggregrates of intracytoplasmic A-type MMTV particles. It should be noted that numerous microvilli are present with budding particles also in evidence. Section C of FIG. 13 shows MJY-alpha cells after treatment with 25 ug PTT.119/ml. for a two (2) hour period. After that treatment period, the layer of cells was washed and then reincubated for one (1) day prior to further processing for electronmicroscopy. Although there are some microvilli with budding particles present, the number of such particles and buds is reduced. Section D of FIG. 13 shows MJY-alpha cells after treatment with 25 ug PTT.119/ml. for two (2) hours. The layer was then similarily washed and reincubated for a two (2) days prior to further processing for electronmicroscopy. Again it can be seen that the number of microvilli has been reduced even farther than from Section C and greatly reduced from the untreated cells shown in Sections A and B. Therefore, as is shown by the contrast between Sections A and B and Sections C and D, treatment with the tripeptide leads to reduced production of the virus within the tumor cells.

EXPERIMENTAL EXAMPLE 14

L-PAM-CROSS-RESISTANCE TEST

Three ascitic leukemia cell lines maintained in BDF$_1$ (BALB/c×DBA/2) mice are used in this example: L1210 leukemia and two L-phenyl-alanine mustard (L-PAM) resistant lines, L1210/L-PAM and P388/L-PAM leukemia. Leukemic cells were harvested, tested for viability, and their cultrues maintained according to stand and techniques.

Three in vitro cultrue adapted lines of L1210 leukemia, the L1210S, L1210DDP and L1210 MTX (used in Example 15) were maintained in logarithmic growth phase in Fischer's medium with 10% horse serum. The L1210DDP cells were 20-fold more resistant to cisplatin than the susceptible L1210S. Likewise, L1210 MTX were 100-times more resistant to methotrexate. The resistance exhibited by both cell lines was stable and the cells were grown in the absence of drugs.

All in vitro PTT.119 and L-PAM treatment of cells were carried out at 37° C. in the appropriate complete growth media containing 10% or 18% sera. L1210, L1210/L-PAM and P388/L-PAM cell suspensions of $1 \times 10^6$ cells/ml were subjected to a single 15, 30 or 60 min pulse exposure to 3.75, 7.5 and 15 uM PTT.119 or L-PAM. Following treatment, media were removed by pelleting the cells at $200 \times g$ for 9 min at 5° C. Cells were then gently washed twice with fresh growth media and finally resuspended in RPMI-1630 medium with 10% FBS for in vitro cultures.

Viability of leukemia cells was ascertained immediately following and every 24 hours after pulse exposure to PTT.119 or L-PAM. During this 7-day period culture media were changed daily by gently pelletting the cells and exchanging 70% of the spent supernatant with fresh media. The viable fraction of cells continuously exposed to drugs was determined once at the end of the 24 hour treatment period. Numbers of viable cells excluding a vital trypan blue stain were enumerated with a haemocytometer by counting all fields for every sample. The means from 20 to 40 evaluations were obtained for each time point and percent viable cells in treated cultures determined by direct comparison with parallel untreated or solvent treated cells. No significant differences were observed in the viabilities of cells treated with solvent or media with no additives, therefore, numbers of control cells are averages of the two experimental controls.

Suspensions of PTT.119 or L-PAM treated cells, and control leukemia cells were adjusted to $1 \times 10^7$ cells/ml based on tumor cell concentrations prior to drug exposure. Syngeneic female $BDF_1$ (BALB/c$\times$DBA/2)f, mice weighing 20 to 26 g received intraperitoneal injections of $1 \times 10^6$ cells. Mice were monitored daily throughout the 45 day examination period and were autopsied at the time of death.

Long-term cultures of L1210 leukemia and MJY-alpha mammary tumor cells were continuously exposed to low doses of PTT.119 by addition of the tripeptide at the time of media replacement. L1210 cells were passaged at $1 \times 10^5$ cells/ml every 3 to 14 days and received 15 to 750 uM PTT.119 at the time of seeding.

MJY-alpha mammary tumor cells were treated with 0.15 to 15 uM PTT.119 at the time of seeding and daily, thereafter, when the medium was changed. The monolayer cultures were passaged every 7 to 21 days. L1210 and MJY-alpha mammary tumor cells exposed to low doses of PTT.119 were periodically tested for susceptibility to 1.5 to 75 uM tripeptide. L1210 cell suspensions were treated for 24 hours as previously described and viable cells enumerated using trypan blue. MJY-alpha cells from treated cultures and parallel untreated controls were seeded at $2 \times 10^5$ cells/2 $cm^2$ while using media containing the appropriate low concentration of PTT.119. One day after plating the confluent layers were treated with additional levels of tripeptide for 24 hours. Cell layers were then released from the substrate with 0.5 ml saline-trypsin-versene, and diluted 2- to 10-fold with trypan blue prior to counting.

Figure 14:
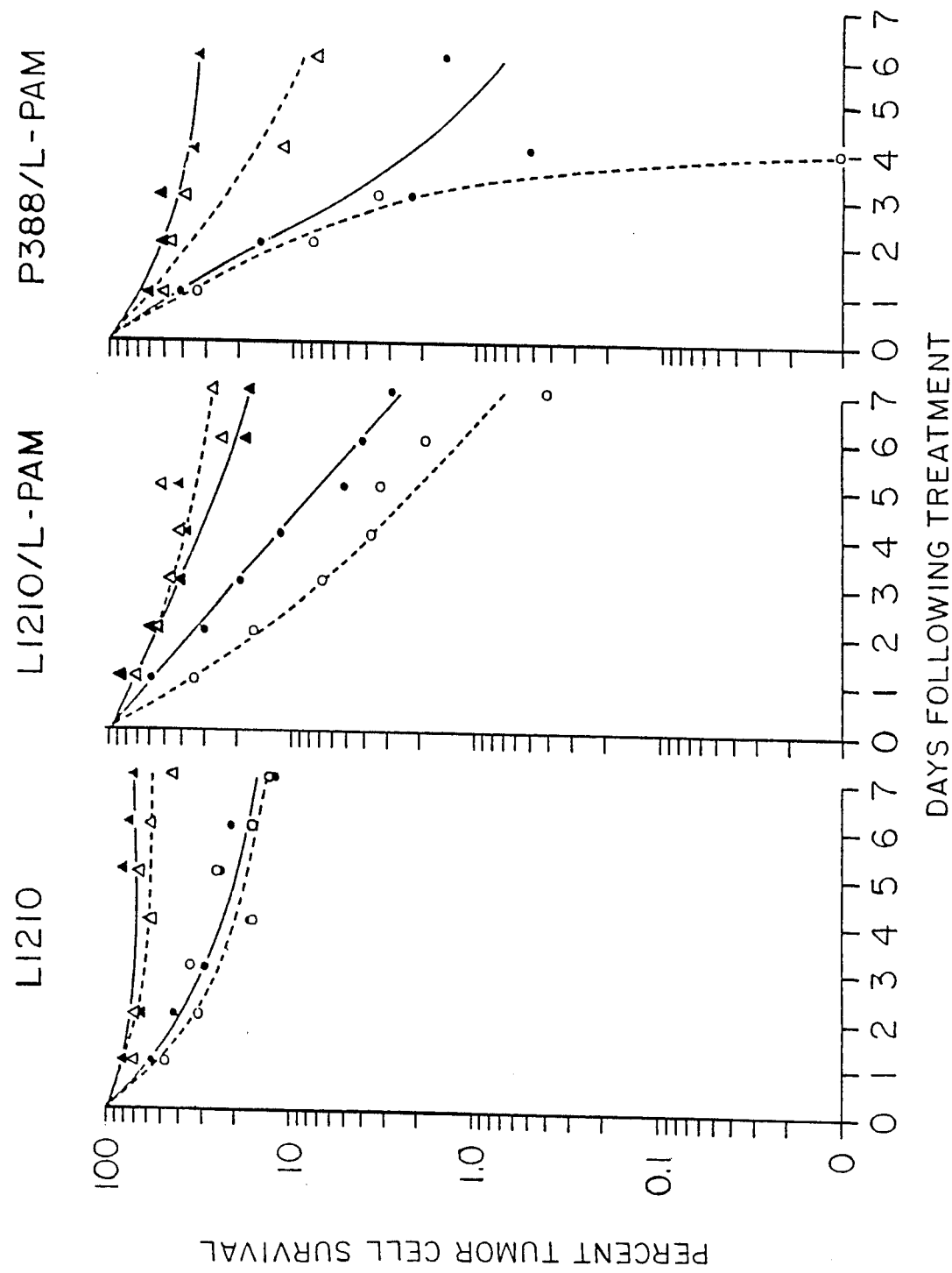
FIG. 14 shows the percent of tumor cell survival related to the number of days following treatment of L1210, L1210 L-pAM and P388/L-PAM leukemia suspensions following exposure to 7.5 uM PTT.119 for 30 (●—●) or 60 (o - - - o) min, or L-PAM for 30 (▲—▲) or 60 (Δ - - - Δ) minutes. Viability data are the means of 20 evaluations with standard deviations of less than 10%, and are representative of values obtained from 2 to 4 other experiments.

Exposure of primary cultures of two L-PAM resistant lines, L1210/L-PAM and P388/L-PAM and the susceptible L1210 leukemia to PTT.119 significantly reduced the fraction of surviving cells. Treatment with 3.75 uM PTT.119 for as short as 30 or 60 min reduced the percentages of viable L1210 and L1210/L-PAM cells to 40–50% and the resistant P388/L-PAM leukemia cells to 0–1% within 4 to 5 days after exposure. In contrast, 80–90% of the L1210, L1210/L-PAM and P388/L-PAM cells remained viable following either a 30 or 60 min exposure to 3.75 uM L-PAM. Both resistant lines as shown in FIG. 14 were markedly more susceptible to 7.5 uM PTT.119 than the L1210 leukemia. The increased cytotoxicity was observed when drug exposure was for either 30 to 60 min and was demonstrable throughout the 6 to 7 day period following PTT.119 treatment. By the end of the examination period the surviving fractions of L1210/L-PAM and P388/L-PAM cells were reduced to 0.8–3% and 0–0.5%, respectively, compared to the 15% for the L1210 cells.

For comparison, the three leukemia lines were treated in parallel with an equimolar dose of L-PAM. Data depicted in FIG. 14 shows that PTT.119 was always more effective. L-PAM was only able to reduce the surviving cell populations of L1210 to 60–80%, L1210/L-PAM to 3–20% and P388/L-PAM cells to 7–40%. Despite the in vivo resistance of L1210/L-PAM and P388/L-PAM tumors to L-PAM, a sizable portion of the tumor cell population is susceptible to the alkylating agent.

Figure 15:
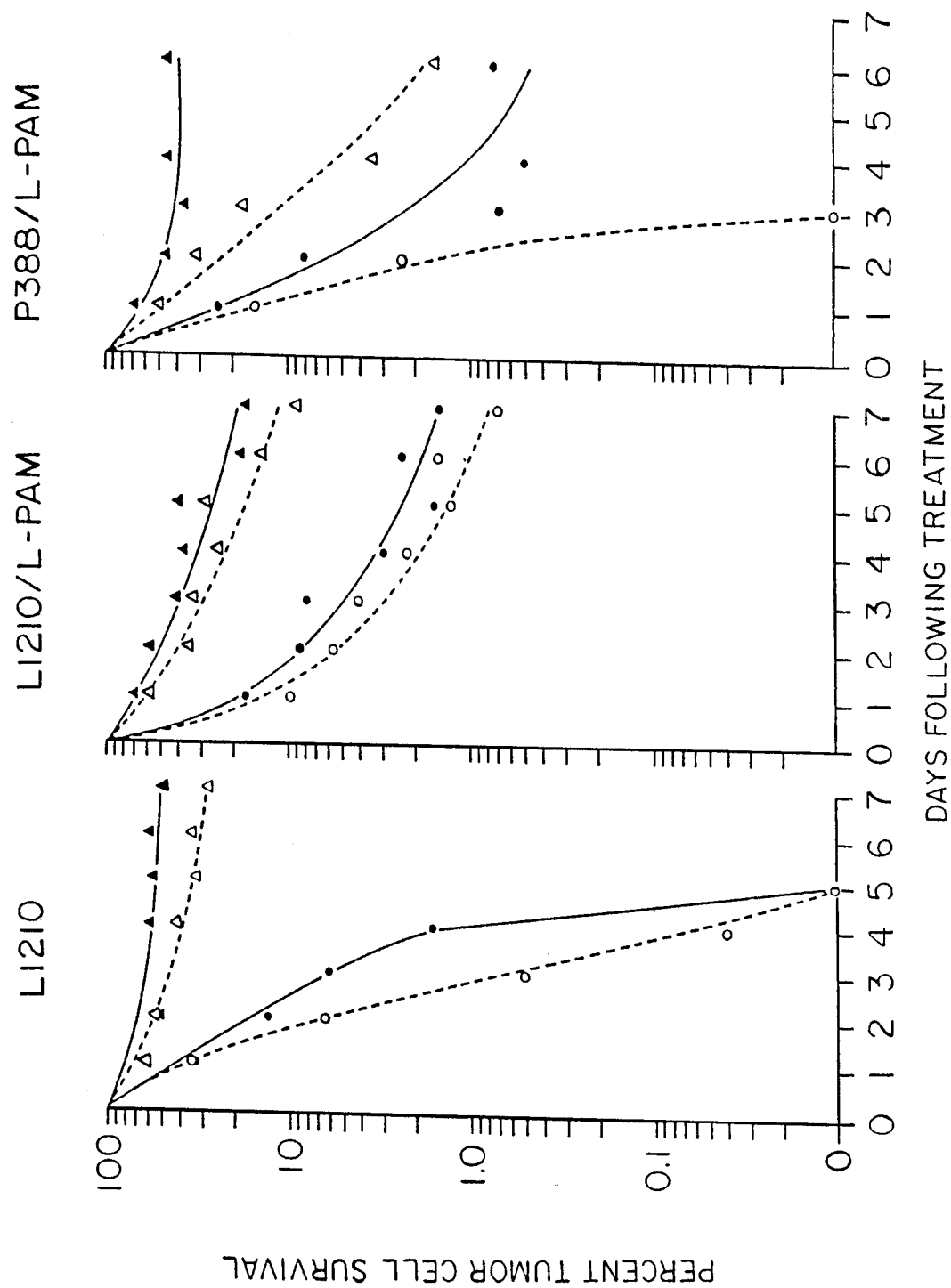
FIG. 15 shows the percent of tumor cell survival related to the number of days following treatment of L1210, L1210/L-PAM and P388/L-PAM leukemia suspensions following exposure to 15 uM PTT.119 for 30 (●—●) or 60 (o - - - o) minutes, or L-PAM for 30 (▲—▲) or 60 (Δ - - - Δ) minutes. Viability data are the means of 20 evaluations with standard deviations of less than 10%, and are representative of values obtained from 2 to 4 other experiments.

Increasing the dosage of PTT.119 to 15 uM resulted in further reductions in cell survivals and also increased the rate of cell cytolysis of all three leukemias as shown in FIG. 15. The most significant change was observed with the L1210 leukemia. Exposure to 15 uM PTT.119 for either 30 or 60 minutes completely eliminated the viable population within 5 days of treatment. Doubling the concentration of L-PAM increased its activity against the leukemia cells particularly when treatment was carried out for 60 minutes although L-PAM still could not eliminate all viable cells.

Figure 16:
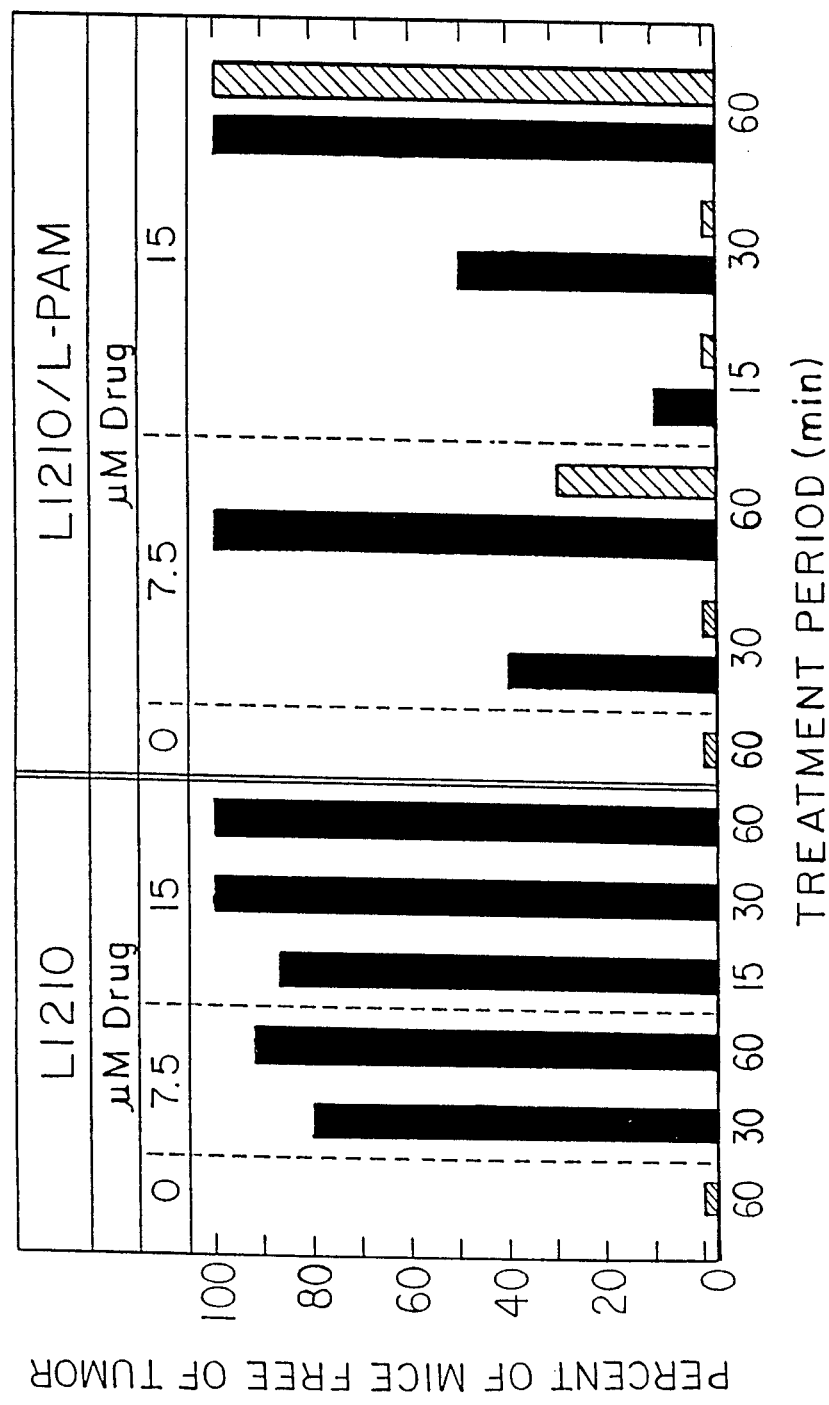
FIG. 16 shows in vivo tumorigenicity of L1210 and L1210/L-PAM leukemia treated with 7.5 or 15 uM PTT.119 (solid bar) or L-PAM (striped bar). Tumor cells were treated for 15, 30 or 60 minutes, washed and $1\times10^6$ cells injected i.p. into BDF$_1$ hosts. Number of tumor free mice were determined 45 days after implantation. Values represent averages of two experiments each containing groups of 10 to 15 mice.

The tumorigenicity of the L1210 and L1210/L-PAM leukemia cells following in vitro treatment with PTT.119 was determined using syngeneic $BDF_1$ recipients. Mice free of tumor were present in every treatment group of both leukemias as shown in FIG. 16 and significant increases in the mean survival time (MST) were also observed in recipients which did succumb to L1210 or L1210/L-PAM tumors as detailed in Table 6.

TABLE 6

MEAN SURVIVAL TIME (MST) OF $BDF_1$ MICE RECEIVING LEUKEMIA CELLS TREATED WITH PTT.119 OR L-PAM

Tumor cells (1 × 10 6/ml) were treated in vitro, washed and implanted into syngeneic hosts. Numbers of surviving animals were determined daily. All values are MST of animals who died of tumor and represent the average of two experiments each containing groups of 10-15 mice.

| Tumor Cell | Drug (uM) | MST in Days TREATMENT PERIOD (min) | | |
|---|---|---|---|---|
| | | 15 | 30 | 60 |
| L1210 | 0 | 10 | 10 | 10 |
| | 7.5 PTT.119 | — | 21[] | 32[] |
| | 15 PTT.119 | 8[f] | TF | TF |
| L1210/L-PAM | 0 | 13 | 13 | 13 |
| | 7.5 PTT.119 | — | 19[**] | TF |
| | 15 PTT.119 | 16[*] | 18[*] | TF |
| | 7.5 L-PAM | — | 15 | 15[f] |
| | 15 L-PAM | 14 | 16 | TF |

[f]Group also contained tumor-free animals
b = Tumor Free
*$p < 0.01$
**$p < 0.001$ PTT.119 at 7.5 and 15 uM was highly effective against L1210 cells. Approximately 80–100% of the mice in every group was free of tumor at the end of the 45-day examination period. The reduction of tumorigenicity of L1210/L-PAM cells increased as the concentration of PTT.119 and the duration of exposure increased. Complete abrogation of L1210/L-PAM tumors was obtained by treatment for 60 minutes with either 7.5 or 15 uM of tripeptide. These results indicate that PTT.119 effectively reduced the population of treated leukemia cells capable of proliferation in the tumor-free mice to 0 since the L.D.$_{100}$ is a single cell. In comparison, in vitro treatment of L1210/L-PAM leukemia with L-PAM resulted in diminution of tumorigenicity only when the cells were treated with 15 uM L-PAM for 60 min. All mice receiving cells treated with either dose of L-PAM for 15 or 30 min died of tumor (FIG. 16) with no observable increase in their MST (Table 6).

Figure 17:
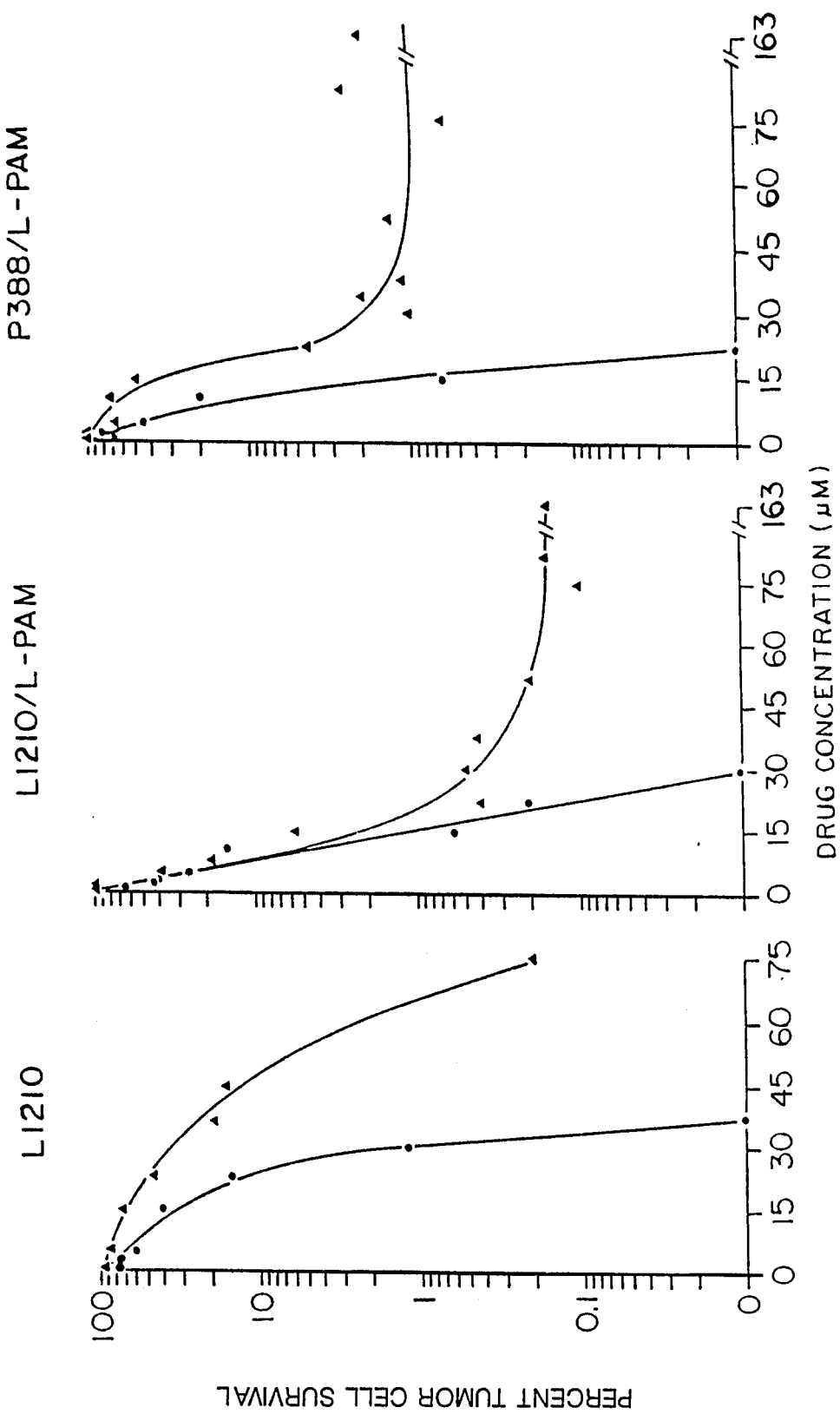
FIG. 17 shows the percent of tumor cell survival related to drug concentration (uM) of L1210, L1210/L-PAM, and P388/L-PAM leukemia suspensions following 24 hour exposure to PTT.119 (●—●) or L-PAM (▲—▲). Data are the means of 30 to 40 evaluations obtained from three experiments.

Treatment of the L-PAM resistant L1210/L-PAM and P388/L-PAM leukemias with increasing doses of PTT.119 for 24 hours revealed that these two tumor lines were more susceptible to the tripeptide than the L1210 leukemia as shown in FIG. 17. As summarized in Table 7, PTT.119 levels which decreased resistant cell survival by 50% (T.C.D.$_{50}$) or totally eliminated viable cells (T.C.D.$_{100}$) were markedly lower compared to those for L1210 cells.

TABLE 7

CYTOLYTIC EFFICACY OF PTT.119 AND L-PAM
L1210, L1210/L-PAM and P388/L-PAM cell suspensions (1 × 10$^6$ cells/ml) were treated for 24 hours and the percentage of viable cells compared to untreated cells and control cells receiving diluent. T.C.D.$_{50}$ and T.C.D.$_{100}$ values represent the means of 25 40 determinations. Viabilities of untreated and solvent treated tumor cells were 98–100%

| Cell Line | T.C.D.$_{50}$ (uM) | | T.C.D.$_{100}$ (uM) | |
|---|---|---|---|---|
| | PTT.119 | L-PAM | PTT.119 | L-PAM |
| L1210 | 9.0 | 22.5 | 37.5 | 75.0§ |
| L1210/L-PAM | 3.0 | 3.8 | 30.0 | 163.0§ |
| P388/L-PAM | 5.0 | 11.0 | 22.5 | 163.0§ |

§Cultures contained 0.2–3% viable cells at 24 hours.

Parallel treatment of the three tumor cell lines with L-PAM demonstrated significant differences between the efficacies of PTT.119 and L-PAM FIG. 17. The cytolytic activity of PTT.119 was always greater than equimolar concentrations of L-PAM. In addition to this quantitative difference, a plateau was observed in the dose response curves the of L1210/L-PAM and P388/L-PAM leukemia treated with L-PAM. A residual number of cells in each of the leukemia populations was unaffected by increasing the L-PAM concentration in excess of 30 uM. As a result the survival of these L-PAM resistant lines could not be completely abrogated and at 163 uM L-PAM approximately 0.2% of the L1210/L-PAM and 3% of the P388/L-PAM populations remained viable (Table 7). The results show that these tumor cell lines maintained in mice are a heterogeneous mixture of both L-PAM susceptible and resistant cells. However, the complete cytolysis of all L1210/L-Pam and P388/L-PAM cells by PTT.119 at concentration similar to the susceptible L1210 leukemia demonstrates the lack of any detectable cross-resistance to the tripeptide.

EXPERIMENTAL EXAMPLE 15

MTX AND CISPLATIN CROSS-RESISTANCE TEST

The cytolytic efficacy of PTT.119 against leukemic cell lines made resistant to the 2,4 diaminofolate antagonist methotrexate (L1210 MTX; T.C.D.$_{50}$ 0.5 uM MTX) and the alkylating agent cis-diamminedichloroplatinum (II) (L1210DDP; T.C.D.$_{50}$ 30 uM cisplatin) was examined and compared to the parental L1210S (T.C.D.$_{50}$ is 5 nM for MTX and 1.5 uM for cisplatin). Methods for harvesting, testing, and maintaining cultures were performed in the same manner used in Example 14.

Figure 18:
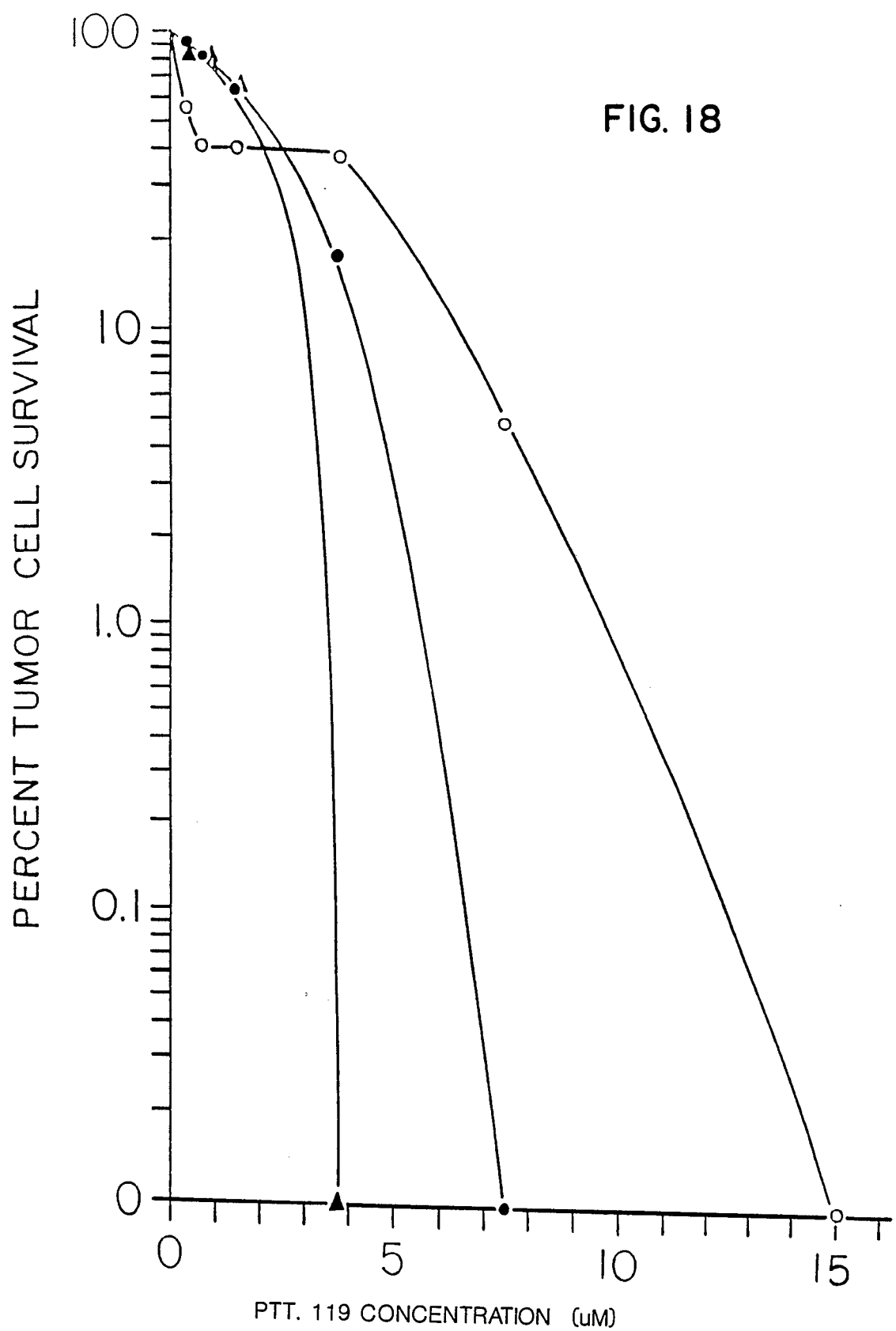
FIG. 18 shows the percent of tumor cell survival related to PTT.119 concentration (uM) of L1210S (●—●), L1210DDP (o—o), and L1210 MTX (▲—▲) leukemia cell lines following 24 hour exposure to PTT.119. Data are the means of three experiments carried out in duplicate.
Figure 19:
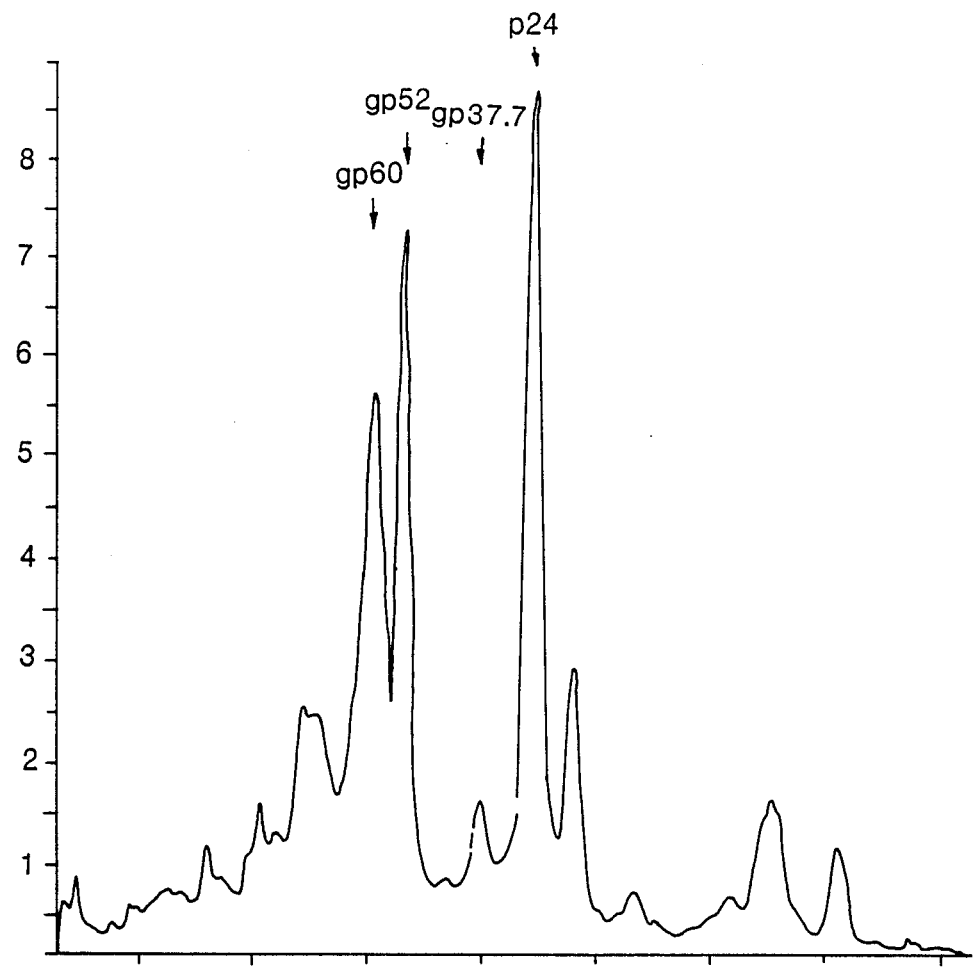
FIG. 19 represents densitometer scans of NaDod-SO$_4$—PAGE of MMTV polypeptides separated on 10–20% acrylamide gradient gels using a discontinuous buffer system and stained with Coomassie Blue. The MMTV is from untreated cultures on day 1.
Figure 20:
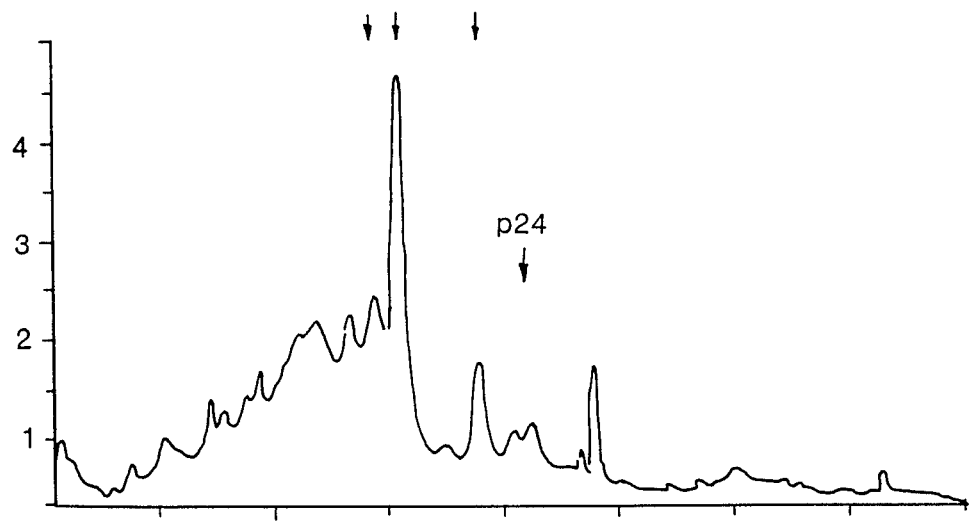
FIG. 20 represents densitometer scans under the same conditions as in FIG. 19 except that the MMTV are from cultures exposed to 15 uM of PTT.119 for 24 hours.
Figure 21:
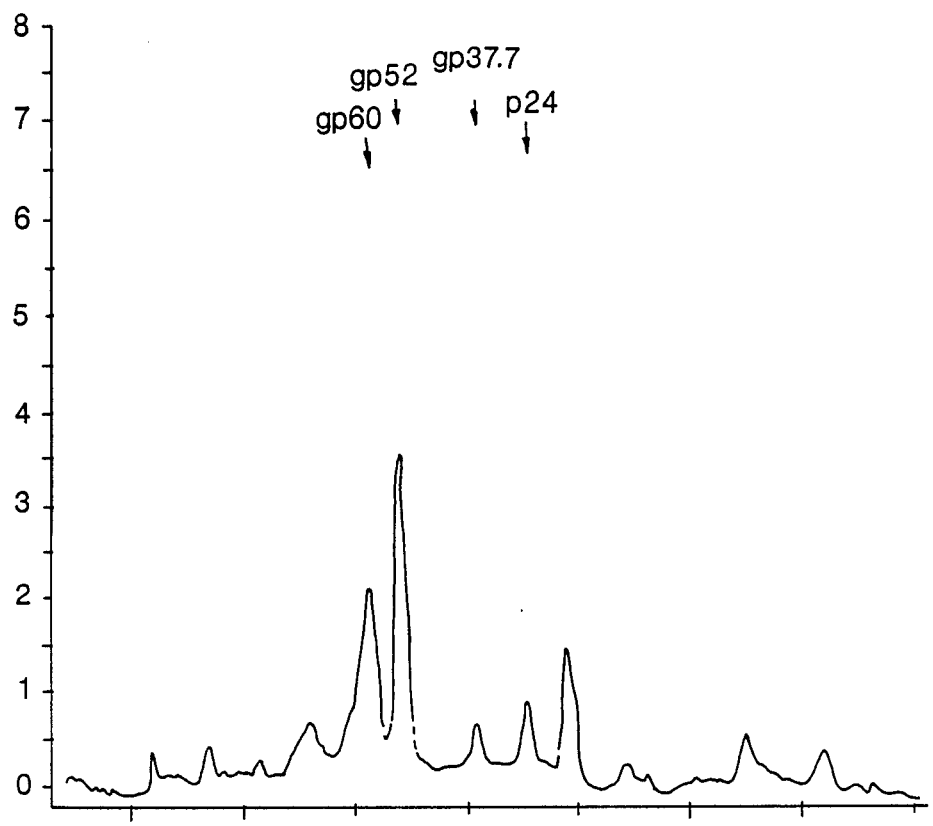
FIG. 21 represents densitometer scans under the same conditions as in FIG. 19 except that the MMTV are from untreated cultures on day 2.
Figure 22:
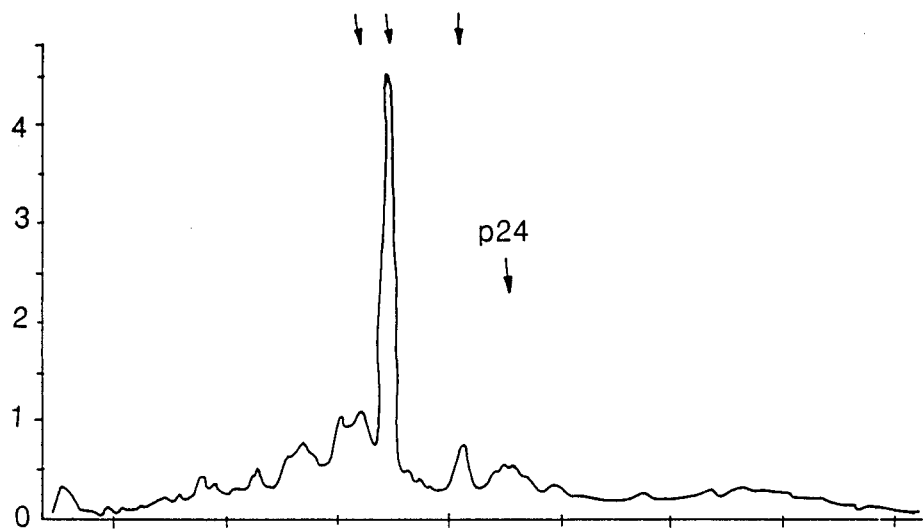
FIG. 22 represents densitometer scans under the same conditions as in FIG. 19 except that the MMTV are from cultures treated with 15 uM PTT.119 for 48 hours.

As shown in FIG. 18 the viability of both resistant lines were decreased in a dose dependent manner following 24 hours exposure to the tripeptide. The L1210 MTX line was more susceptible in comparison to the L1210S leukemia; the T.C.D.$_{50}$ and T.C.D.$_{100}$ or L1210 MTX were 1.94 uM and 3.75 uM, respectively, compared to 2.38 uM (T.C.D.$_{50}$) and 7.5 uM (T.C.D.$_{100}$) for the L1210S. The L1210DDP line was also completely susceptible to PTT.119 although the dose response curve indicates the existence of at least two subpopulations of leukemic cells with varying sensitivities to the tripeptide. Approximately 60% of the L1210DDP leukemic cells were highly susceptible to PTT.119 doses of 1 uM (T.C.D.$_{50}$ 0.525 uM) with the remaining population becoming sensitive to the tripeptide at 4–15 uM. The small plateau in cell viability was consistently observed in every trial with the tripeptide. The data suggests that the cloned population of L1210DDP which displays a homogeneous response to cisplatin treatment is heterogenous with respect to its sensitivities to another alkylating agent.

EXPERIMENTAL EXAMPLE 16

PTT.119 INDUCED RESISTANCE TEST

The ability of PTT.119 to induce drug resistant cells was examined by maintaining tumor cell lines in the presence of low concentrations of the tripeptide. The first series of these experiments involved continuous treatment of the susceptible MJY-alpha cells (T.C.D.$_{50}$ 1.5, 7.5 or 15 uM PTT.119). Monolayers grown in the presence of 15 uM PTT.119 did not survive beyond the second passage. MJY-alpha cells exposed to the three lower concentrations of PTT.119 were successfully maintained for 8 months. The growth rates of these treated cells (alpha-0.15, alpha-1.5, alpha-7.5) were diminished resulting in their subculture every 1.5–2 weeks compared to the weekly passage of the untreated parental cells. The susceptibility of alpha-0.15, alpha-1.5 and alpha-7.5 to PTT.119 was tested periodically by 24 h exposure to six concentrations of the tripeptide (1.5, 3.75, 7.5, 15, 37.5 and 75 uM). No alteration in the dose response curves of the three PTT.119-treated lines were observed compared to previously untreated MJY-alpha cells.

Long-term in vitro suspension cultures of L1210 leukemia cells have also been continuously treated with PTT.119 at 15, 75, 150, and 1500 nM. Cells treated with tripeptide doses of 75 nM or greater were all rendered nonviable within the first 3 or 4 subcultures. Two cell lines L1210-T1 and L1210-T2 were maintained in 15 nM PTT.119 for 28 and 23 passages, respectively. The dose responses of L1210-T1 and L1210-T2 cells at 24 hours PTT.119 treatment was repetitively tested. An increase in resistance to PTT.119 at the concentrations of 15 and 22.5 uM was observed in both lines between the 8th and 16th passages. At these two doses, PTT.119 cytotoxicity was found to be 20–30% lower compared to untreated L1210 cells. However, resistance was not stable and by the 20th passage no differences could be detected in the dose response curves of L1210; L1210-T1 and L1210-T2.

Further attempts to induce an L1210 line resistant to PTT.119 by escalation of tripeptide dosage were caried out. At the 29th passage of L1210-T1, the concentration of PTT.119 was increased to 37.5 nM. Characterization of the dose response of L1210-T1 maintained at this higher concentration for 25 passages has demonstrated that thus far no resistant L1210 cells have been induced by the tripeptide. Further escalation of the tripeptide concentration to 52.5 nM rendered the L1210-T1 cells nonviable within 6 subcultures. These studies using the L1210 leukemia and the MJY-alpha mammary tumor cell line demonstrate that resistance to PTT.119 is very difficult to induce and strongly indicates that inclusion of carrier amino acids in the parental bis-(2-chloroethyl) amino bifunctional alkylating moiety renders the tripeptide an extremely poor mutagen.

We hypothesize that the observed increase in PTT.119 cancericidal activity is related to the structural alteration of the parental m.L.SL molecule which contains the bis-(2-chloroethyl)amino bifunctional akylaing moiety. The evidence sugests that linkage of phe and met in the L configuration to the amino- and carboxyl-groups of the phe residue of m.L.SL alters and/or increases the transport of PTT.119 across the tumor cell membrane. This change in PTT.119 transport could account for the increased cytolytic efficacy of the tripeptide compared to m.L.SL or its structural isomer L-PAM observed in this investigation.

EXPERIMENTAL EXAMPLE 17

EFFECTS OF CONTINUOUS PTT.119 TREATMENT ON MMTV PRODUCTION

Confluent 4 to 7 day old monolayer cultures ($10^6$ cells/ml) were treated with PTT.119 for between 30 minutes and 48 hours at 37° C. Continuous 48 hour exposure was accomplished by exposing monolayers to 1.5, 7.5 or 15 uM PTT.119. Spent media were removed after 24 hours for viral harvest and replaced with fresh media containing the tripeptide. MMTV were radiolabeled with [$^3$H]-leucine (4 uCi/ml) during the first 24 hours with [$^{35}$S-methionine (3 uCi/ml) between 24 to 48 hours.

Monolayer cultures were also treated for between 0.5 and 2 hours with 7.5, 15, or 37.5 uM PTT.119. Following treatment, PTT.119 was removed by rinsing the monolayers twice with treatment medium. Cells were then radiolabeled with [$^{35}$S]-methionine (4 uCi/ml) in treatment medium for 24 hours. MMTV was harvested and cultures chased with unlabeled treatment medium for another 24 hours. The virus was again harvested and the cells reincubated with hydrocortisone-free growth medium containing 18% FBS. The media were changed daily for 5 days. Cells were then given growth medium with hydrocortisone for 24 hours before labeling with [$^3$H]-leucine (4 uCi/ml) in treatment medium. MMTV was again harvested after 24 hours. The spent media were clarified and MMTV concentrated by pelleting. Virions were purified using discontinuous and isopycnic sucrose gradients.

The viability of MJY-alpha mammary tumor cells were determined by releasing the cell layers from the substrate with saline-trypsin versene and quantifying the cells excluding the Trypan blue vital due. Values from duplicate or triplicate treated and parallel control cultures were averaged for each time point. Percentages of viable treated cells were determined by direct comparison of these cultures to experimental control cultures receiving medium or medium and solvent.

The metabolism of treated MJY-alpha mammary tumor cell cultures were screened by monitoring the uptake and incorporation of 3H-uridine, 3H-thymidine, and 35S-methionine. Cultures were treated as described and given radiolabeled precursors in treatment medium at 0–24 for 24 to 48 hours during the treatment periods.

Levels of radioactivity incorporated into the cells were determined following harvesting of the cells on glass filters using a Mash II cell harvester. Each sample was examined in quadruplicate.

Extracellular MMTV was quantitated using a modification of a direct Enzyme-Linked Immunosorbent Assay (ELISA) technique devised by Khan et al. (1982). Nunc immunoplates were sensitized with MMTV preparations disrupted in 2% NP-40 and serially diluted in 0.15M $Na_2CO_3$-0.035M $NaHCO_3$ buffer, pH 8.6, by incubation in a moist chamber for 18 hours at 4° C. Wells were washed three times between all procedural steps with 0.01M phosphate-buffered-saline with 0.5% Tween 80, pH 7.4 (Pi/Na/Tween). Sensitized wells were then sequentially subjected to 1 hour incubations with (1) 0.5% bovine serum albumin in Pi/NaCl/Tween (4° C.), followed by either (2) preimmune rabbit sera or multivalent anti-MMTV antisera diluted 1:50 in Pi/NaCl/Tween at 37° C., and finally (3) a 1:1000 dilution of alkaline phosphatase-conjugated goat anti-rabbit IgG (Dynatech, Inc.) at 37° C. Reactions were terminated with 25 ul of 3N NaOH after incubation for 1 to 2 hours at 37° C. Intensity of the color reactions were determined at 410 nM using a Dynatech ELISA plate reader. The detection limit of the assay was 3–5 ng MMTV protein per well.

Intracellular MMTV proteins were identified in monolayer cells after 24 or 48 hour exposure to 15 uM PTT.119. Cultures were labeled with 25 uCi/ml of ($^3$H)-leucine for the first 24 hours and were then doubly labeled with ($^{35}$S)-methionine when the spent media were replenished. The relative rates of MMTV polypeptide synthesis were determined using parallel cultures continuously-treated with PTT.119 and pulse labeled for 15 minutes with $^{35}$S-methionine. Following labeling, the cells were washed twice in cold 0.01M phosphate-buffered saline, pH 7.5, and a solution of protease inhibitors added to yield a final concentration of 1 uM pepstatin, 10 ug soybean trypsin inhibitor/ml, and 1 mM N-ethyl maleimide. Cells were then disrupted in 0.05M phosphate buffer containing 0.1M NaCl and 0.1% Triton X-100, pH 7.5 (Pi/NaCl/Triton). Cells were scraped from the substrate and lysis completed by passing the suspensions through a 27 gauge needle five times. Nuclei were removed by centrifugation at 600×g for 10 minutes at 4° C. and 100 ul aliquots of the supernatants mixed with 10 ul preimmune rabbit sera and 50 ul of 10% (x/v) formalin-fixed and heat-killed.

Following a 15 minute incubation at 26° C., the *Staphlococcus aureus* (Cowan strain) immunoabsorbent was removed by centrifugation at 10,000×g for 1 minute in a Beckman microfuge. Supernatants (100 ul) were sequentially incubated at 26° C. with 33 ul of rabbit anti-MMTV antisera for 25 minutes and 150 ul of 10% *S.* aureus for 15 minutes. S. aureus was then pelleted and the precipitate washed five times in Pi/NaCl/Triton. Samples were finally resuspended in 20 ul of 1% NaDodSO$_4$/2-mercaptoethanol, heated for 1 minute at 100° C. to release MMTV proteins, and centrifuged to remove S. aureus. Supernatants were then subjected to NaDodSO$_4$-PAGE. Samples were disrupted in 1% NaDodSO$_4$ and 1% B-mercaptoethanol at 100° C. for 1 minute electrophoresed on 10–20% polyacrylamide gradient slab gels using a discontinuous buffer system. Electrophoresis of immune precipitates from cell lysates was carried out in a similar manner using 7.5–15% polyacrylamide gradients. M$_r$ of MMTV-related polypeptides were determined by coelectrophoresis of [$^{14}$C]-protein standards (M$_r$ 30,000 to 50,000 Da; New England Nuclear). Radioactivity was determined and the levels associated with MMTV polypeptide peaks quantitated using a generalized curve-fit computer program.

The effects of PTT.119 on MMTV replication were examined following continuous 24 and 48 hour exposure of MJY-alpha monolayer cultures to the tripeptide. Inclusion of radiolabeled leucine and methionine in the treatment medium revealed decreases in de novo synthesis of extracellular MMTV particles (Table 8). Reductions in MMTV production were observed within 24 hours of exposure to the tripeptide and appeared to be dose-dependent. MMTV synthesis was unaffected by 1.5 uM PTT.119, only slightly depressed by 7.5 uM PTT.119, but was significantly reduced by exposure to 15 uM tripeptide. At the highest PTT.119 concentration, MMTV synthesis was less than 70%, compared to parallel control cultures after 24 hours, and was further decreased to 30% following an additional day of treatment. In contrast, exposure of MJY-alpha cells to 15 uM L-PAM induced a transient inhibition of MMTV synthesis. The initial decrease in extracellular MMTV due to L-PAM was equivalent to the level observed following 24 hour exposure to the tripeptide. However, continued L-PAM exposure did not increase nor did it maintain the initial depression of MMTV production. After 48 hours of 15 uM L-PAM treatment, MMTV production increased to 97% of control levels.

TABLE 8

| | MMTV PRODUCTION | |
|---|---|---|
| | Relative level of MMTV produced (%)[a] | |
| Compound | Treatment Period | |
| (uM) | 24 hours | 48 hours |
| Solvent[b] | 100 | 100 |
| PTT.119: | | |
| 1.5 | 104.9 | 94.0 |
| 7.5 | 91.5 | 92.8 |
| 15.0 | 68.7 | 29.5 |

TABLE 8-continued

| | MMTV PRODUCTION | |
|---|---|---|
| | Relative level of MMTV produced (%)[a] | |
| Compound | Treatment Period | |
| (uM) | 24 hours | 48 hours |
| L-PAM: 15.0 | 71.7 | 96.5 |

[a]MJY-alpha cell layers received fresh labeling medium with drugs or solvent at time 0 and after 24 hr of treatment. $^3$H-leucine was also included during the first 24 hr of treatment and was replaced with $^{35}$S—methionine between 24–48 hr. MMTV was purified as described and the relative level of virus production determined by comparison of radiolabeled incorporation. Values were obtained from 2–3 separate experiments.
[b]Solvent volume was equivalent to the addition of 15.0 uM PTT.119.

Cellular viability and metabolism were examined in order to ascertain if the PTT.119-induced reductions in MMTV production could be distinguished from the general antitumor cell activity of the tripeptide. Confluent MJY-alpha monolayers were stimulated with hydrocortisone prior to continuous 24 and 48 hours treatment with PTT.119, L-PAM, or solvent to mimic the conditions used during viral harvests. As shown in Table 9, reductions in cell numbers were detected within 24 hours of exposure to 7.5 and 15 uM PTT.119.

TABLE 9

| | TUMOR CELL LAYER VIABILITY | |
|---|---|---|
| | Viability compared to control cultures (%)[a] | |
| Compound | Treatment period | |
| (uM) | 24 hour | 48 hour |
| Solvent[b] | 100 | 100 |
| PTT.119: | | |
| 1.5 | 106 | 104.9 |
| 7.5 | 83.2 | 103.0 |
| 15.0 | 91.0 | 85.4 |
| L-PAM: 15.0 | 101 | 96.9 |

[a]Viability of solvent and drug-treated cultures were compared to untreated cells.
[b]Volume of solvent was equivalent to addition of 15.0 uM PTT.119.

The number of viable cells was unaffected at the lowest tripeptide concentration of 1.5 uM. Viability of the tumor cell layers was reduced by 15–20% compared to cultures receiving solvent. However, continued tripeptide treatment for 48 hours did not result in further decreases in the number of viable cells and tumor cell survival was 103% and 85% for cultures treated with 7.5 and 15 uM PTT.119, respectively. No significant decrease in viability was observed when the cells were exposed to 15 uM L-PAM.

In addition to determining cellular viability by trypan blue exclusion, the levels of metabolic activity of PTT.119-treated cells were compared to solvent-treated and untreated controls. Confluent MJY-alpha monolayers were again processed as previously described and $^3$H-uridine, $^3$H-uridine, $^3$H-thymidine, and $^{35}$S-methionine incorporation quantitated during the 24 and 48 hour treatment periods. Following 24 hour tripeptide treatment, the only parameter that was substantially depressed compared to control cultures was the incorporation of $^{35}$S-radioactivity into cells treated with 15 uM PTT.119 (Table 10).

TABLE 10

| | INCORPORATION OF RADIOLABELED PRECURSORS | | | | | |
|---|---|---|---|---|---|---|
| | Relative level of incorporation of radiolabels (%)[a] Treatment period | | | | | |
| Compound | 24 hours | | | 48 hours | | |
| (uM) | $^3$H—ur | $^3$H—thy | $^{35}$S—met | $^3$H—ur | $^3$H—thy | $^{35}$S—met |
| Solvent[b] | 100 | 100 | 100 | 100 | 100 | 100 |
| PTT.119: | | | | | | |

TABLE 10-continued

| Compound | INCORPORATION OF RADIOLABELED PRECURSORS | | | | | |
|---|---|---|---|---|---|---|
| | Relative level of incorporation of radiolabels (%)[a] Treatment period | | | | | |
| | 24 hours | | | 48 hours | | |
| (uM) | $^3$H—ur | $^3$H—thy | $^{35}$S—met | $^3$H—ur | $^3$H—thy | $^{35}$S—met |
| 1.5 | 90.9 | 91.2 | 103.3 | 103.4 | 118.1 | 96.1 |
| 7.5 | 100.6 | 99.0 | 97.2 | 108.6 | 83.1 | 89.9 |
| 15.0 | 100.1 | 103.6 | 82.7 | 80.5 | 82.9 | 80.4 |

[a]MJY-alpha cell layers received fresh labeling medium with drugs or solvent at time 0 and after 24 hr of treatment. $^3$H—uridine, $^3$H—thymidine and $^{35}$S—methionine were included at 0-24 or 24-48 hr. Levels of radiolabel incorporation were compared following harvesting of the monolayers as described in the Materials and Methods. Data are derived from the average of eight samples per value.
[b]Solvent volume was equivalent to the addition of 15 uM PTT.119.

No significant alterations in incorporation were observed in cultures treated with 1.5 and 7.5 uM PTT.119. During the second day of treatment with 15 uM PTT.119, the incorporation of all three precursors was decreased as demonstrated by the 20% reductions in levels of cell-associated radioactivity. Cells treated with 1.5 uM PTT.119 continued to appear unaffected by the drug, whereas, $^3$H-thymidine incorporation into cultures receiving 7.5 uM PTT.119 was depressed by 17%.

The intracellular synthesis and processing of MMTV proteins during PTT.119 treatment was quantitated by the inclusion of radiolabeled amino acid residues. After 24 or 48 hours of exposure to PTT.119 cell lysates were prepared and subjected to immune precipitation with antisera against MMTV virion polypeptides. Quantitation of all radiolabeled MMTV antigens in immune precipitates of cells labeled for 24 hours revealed that the levels of intracellular MMTV polypeptides were higher in cells treated for 24 or 48 hours with 15 uM PTT.119 compared to control cells (Table 11).

TABLE 11

RELATIVE LEVELS OF MMTV-ASSOCIATED
RADIOACTIVITY (%) TREATMENT PERIOD

| | 24 hr | | 48 hr | |
|---|---|---|---|---|
| Intracellular MMTV Polypeptides[a] | Control | 15 uM PTT.119 | Control | 15 uM |
| 24 hr labeling period[b]: | [33,881] | [43,514] | [62,745] | [78,973] |
| Total MMTV Protein[d] | 100 | 128 | 100 | 125 |
| Pr$^{gag}$/pol[e] | 60.9 | 60.9 | 75.2 | 69.7 |
| Pr$^{73}$ env | 138 | 7.2 | —[f] | — |
| gp60; gp52 | 15.6 | 20.2 | 19.6 | 23.6 |
| p24 | 2.5 | 3.8 | 3.5 | 2.4 |
| p17, p13 | 7.2 | 7.9 | 1.7 | 4.3 |
| 15 min pulse labelling[c] | [58,422] | [105,814] | [165,802] | |
| Total MMTV Protein[d] | 100 | 181 | 100 | 154 |
| Pr$^{gag}$/pol[e] | 82.2 | 83.2 | 84.2 | 80 |
| Pr$^{73}$ env | — | — | — | — |
| gp60, gp52 | 12.7 | 10.6 | 8.9 | 10.6 |
| p24 | 1.8 | 1.5 | 3.5 | 3.3 |
| p17, p13 | 3.3 | 4.7 | 3.4 | 6.3 |

[a]Intracellular MMTV polypeptides were obtained from cellular lysates of confluent MJY-alpha monolayers by immune precipitation with rabbit-anti MMTV antisera. Precipitates were subjected SDS-PAGE for further identification of MMTV proteins.
[b]Cell layers were labeled with $^3$H—leucine (0-24 hr) or with $^{35}$S methione (24-48 hr) during PTT.119 treatment.
[c]Cell layers were pulsed for 15 min with $^{35}$S—methionine after 23.75 or 47.75 hr of PTT.119 treatment.
[d]Radioactivity associated with all intracellular MMTV proteins were quantitated and compared; values in brackets are mean dpm levels of samples.
[e]Pr$^{gag/pol}$ consists of following MMTV precursors and proteins: Pr160$^{gag/pol}$, Pr110$^{gag}$, Pr94$^{gag}$, Pr77/75$^{gag}$, Pr38$^{gag}$, P44/Pr43
[f]Glycosylated precursor, Pr$^{73env}$ is labeled poorly with $^{35}$S—methionine.

This indicates that either the rate of MMTV synthesis was higher in PTT.119-treated cells or that particle maturation and virion release from the cells were depressed causing an accumulation of intracellular proteins.

Examination of MMTV proteins by pulse labelling of the cells for 15 minutes at the end of the 24 and 48 hour treatment periods also revealed apparent increases in the de novo synthesis of MMTV proteins (Table 11). The levels of radiolabeled MMTV polypeptides were 1.5-fold higher in PTT.119-treated cells than in parallel controls. These relatively rapid increases in intracellular levels of viral proteins suggest that PTT.119 exposure increased the overall rates of MMTV transcription and/or translation.

Comparison of the relative levels of individual MMTV poly-protein precursors and polypeptides revealed no significant differences between MMTV proteins from solvent and PTT.119-treated cultures (Table 11). The contributions of the MMTV polypeptides to the total pool of virion proteins were relatively constant over the 2 day exposure period when examined by radiolabeling for either 24 hours or for a short 15 minute pulse. Apparently the tripeptide does not significantly alter early steps in protein cleavage and processing of the glycosylated and nonglycosylated MMTV precursors.

EXPERIMENTAL EXAMPLE 18

EFFECTS OF PTT.119 ON MMTV POLYPEPTIDES

Extracellular MMTV particles produced by PTT.119-treated cells were examined to ascertain if the tripeptide induced any alterations in their polypeptide composition. MMTV purified from monolayer cultures treated with 1.5, 7.5, or 15 uM PTT.119 for 24 or 48 hours were disrupted and subjected to NaDosO$_4$-PAGE. Representative profiles of these virus preparations quantitatively obtained from parallel cultures again demonstrated as illustrated by FIGS. 19 through 22 a depression in MMTV production with exposure to 15 uM PTT.119. In addition, profiles of MMTV particles from these cultures demonstrated that the tripeptide induced substantial decreases in the levels of the nonglycosylated protein, p24. Similar studies using 7.5 uM, but not 1.5 uM tripeptide, also revealed diminution of the p24 protein located in the virion core.

In order to better define the observed changes in the viral proteins, MJY-alpha cultures were suquentially labeled with $^3$H-leucine and $^{35}$S-methionine every 24 hours of treatment with 15 uM PTT.119. Quantitation of the relative levels of radioactivity associated with MMTV polypeptides confirmed the reductions observed on the coomassie blue stained gel preparations (Table 12). Within the first 24 hours of PTT.119 treatment, the level of p24 was decreased by 36% compared to virions from cultures receiving solvent. This reduction in p24 increased to 71% after an additional 24 hours of PTT.119 treatment. Consistent alterations in two virion glycoproteins were also observed during the 48 hour treatment period. The relative levels of gp60 increased 1.3 to 1.6-fold whereas, gp37.7/33 was reduced by 13 to 24% compared to controls. Minor fluctuations in the amounts of the other viral proteins were also detected, but these changes were inconsistent.

In contrast, the polypeptide profiles of MMTV obtained from MJY-alpha cultures treated with 15 uM L-PAM were relatively similar to virions from controls monolayers (Table 12). Comparison of the relative levels of MMTV polypeptides in the virions after 24 and 48 hour or treatment also revealed decreases in p24 although the redu reductions were significantly less than that observed with the tripeptide. Alterations in the levels of gp60 and gp37.7/33 were also detected, but they were small and fluctuated among different preparations.

medium containing hydrocortisone for the next 2 days. Regular growth medium was then used on days 2 through 5 which was again replaced on days 5 through 7 with medium containing hydrocortisone. The levels of extracellular MMTV antigens produced on days 1 through 2, 2 through 3, and 6 through 7 were determined by ELISA. As shown in Table 13, all cultures exposed to PTT.119 produced less MMTV proteins than controls. These decreases were related to the dose and duration of PTT.119 exposure.

TABLE 13

MMTV PRODUCTION BY CULTURES PULSE-TREATED WITH PTT.119 ug MMTV protein/75 cm² flask (% of control level)[a]

| Day after treatment | Control[b] | 15 uM PTT.119 | | 37.5 uM PTT.119 | |
|---|---|---|---|---|---|
| | | 2 hr | 4 hr | 0.5 hr | 1.0 hr |
| 1 | 20.6 | 16.0 (78) | 16.7 (81) | 14.4 (70) | 11.0 (53) |
| 2 | 19.3 | 12.3 (64) | 11.9 (62) | 11.0 (57) | 11.2 (58) |
| 7 | 35.2 | 11.0 (31) | 7.6 (22) | 5.8 (16) | 0.9 (3) |

[a]Confluent MJY-alpha cell layers were pulse treated, washed and reincubated in drug-free medium. Levels of MMTV proteinproduced were determined by the ELISA method described in Materials and Methods. The values represent the average of 3–4 determinations of 4 separate experiments.

[b]Parallel controls were carried out in each experiment. No significant differences were detected among the samples and these values represent the average of all the experiments.

TABLE 12

Percentage of Radioactivity Associated with each Polypeptide[a]

| MMTV Polypeptides | [³H] Leu (0–24 hr) | | | | | [35S] met (24–48 hr) | | | |
|---|---|---|---|---|---|---|---|---|---|
| | Control | 15 uM PTT.119 | | 15 uM L-PAM | | Control | 15 uM PTT.119 | 15 uM L-PAM | |
| gp 60 | 20.1 | 25.6 | | 20.4 | | 19.3 | 31.4 | 21.2 | +10 |
| gp 52 | 25.5 | 24.9 | | 25.4 | | 18.0 | 18.9 | 19.8 | |
| gp 37.7/33 | 25.3 | 22.0 | | 28.6 | | 29.4 | 18.6 | 21.7 | −11 |
| p 24 | 13.1 | 8.4 | (64%) | 10.5 | (80.2) | 23.6 | 69 (29.2) | 19.2 | (81.4) |
| p 22 | 4.0 | 4.0 | | 3.7 | | 4.2 | 9.7 | 4.9 | |
| p 17 | 4.3 | 6.9 | | 3.6 | | 3.5 | 5.4 | 5.6 | |
| p 13 | 4.1 | 4.4 | | 4.2 | | 3.8 | 5.3 | 4.2 | |
| p 8 | 3.6 | 3.8 | | 3.6 | | 3.2 | 3.8 | 3.4 | |

MJY-alpha cultures were treated with medium containing 15 uM drug and 3H—leucine (4 uCi/ml), virions were harvested after 24 hr and the cultures given fresh medium with 15 uM and ³⁵S—methionine (3 ul:/uC). MMTV. Percentages are based on quantitation of radioactive peaks of MMTV polypeptide separated by SDS-PAGE in 2–5 experiments.

EXPERIMENTAL EXAMPLE 19

EFFECTS OF PULSE PTT.119 TREATMENT

A series of experiments were carried out to ascertain whether alterations in MMTV production and composition required the continued presence of the tripeptide. The first study extended the previous investigations of MMTV production by MJY-alpha cell layers exposed to 15 uM PTT.119 for 48 hours. Following PTT.119 treatment (days 0–2), confluent MJY-alpha layers were washed and reincubated in growth medium for 48 hours (days 2–4) and growth medium with hydrocortisone for 24 hours (day 4–5) before labeling with ³⁵S-methionine on day 5. After 24 hours MMTV production in parallel cultures previously treated with PTT.119 or solvent were determined and compared. Quantitation of ³⁵S-radioactivity present in purified viral preparations revealed that MMTV production in the treated cultures remained depressed at 50–55% of control. Further NaDodSO₄-PAGE analyses of the viral proteins also demonstrated the continued reduction of the p24 protein. The relative level of this polypeptide remained at 35–40% compared to control.

Cell layers were also pulsed with solvent or 15 uM PTT.119 for 2 or 4 hours, or with 37.5 uM PTT.119 for 0.5 or 1 hour. MJY-alpha cultures were then washed twice and reincubated with daily changes of growth Reduction in MMTV production continued and increased over the 7 day period. The MMTV levels in treated cultures were lowest 6 days after pulse exposure. The data indicate that MMTV synthesis is not immediately restored following removal of PTT.119 and suggests that the tripeptide-induced inhibition of MMTV production can escalate with time.

The polypeptide profiles of MMTV produced by MJY-alpha cells following a 1 hour exposure to 15 uM PTT.119 were also examined 1, 2, and 7 days after treatment. Addition of radiolabeled precursors again demonstrated reductions in MMTV production which continued for 1 week after PTT.119 treatment. Compared to virions from control cultures, the relative levels of MMTV from treated cell layers decreased from 96.6% on day 1 to 63% and 54% on days 2 and 7, respectively (Table 14).

TABLE 14

Percentage of Radioactivity Associated with MMTV Polypeptides After a 7 hr Exposure to 15 uM PTT.119

| MMTV Polypeptides | Day 1 | | Day 2 | | Day 7 | |
|---|---|---|---|---|---|---|
| | Control | PTT.119 | Control | PTT.119 | Control | PTT.119 |
| gp 60 | 24.6 | 22.5 | 20.1 | 21.7 | 22.5 | 25.3 |
| gp 52 | 22.8 | 21.1 | 19.2 | 22.4 | 23.4 | 23.5 |
| gp 37.7/33 | 26.2 | 22.2 | 26.4 | 28.1 | 27.2 | 26.8 |
| p 24 | 12.7 | 11.1 (86) | 18 | 6.7 (37.2) | 13.5 | 8.7 (64.4) |

TABLE 14-continued

Percentage of Radioactivity Associated with MMTV Polypeptides After a 7 hr Exposure to 15 uM PTT.119

| MMTV | Day 1 | | Day 2 | | Day 7 | |
|---|---|---|---|---|---|---|
| Polypeptides | Control | PTT.119 | Control | PTT.119 | Control | PTT.119 |
| p 22 | 4.5 | 9.7 | 4.7 | 7.2 | 6.1 | 6.0 |
| p 17 | 2.7 | 3.2 | 3.5 | 5.5 | 2.8 | 3.5 |
| p 13 | 3.3 | 5.5 | 5.7 | 5.6 | 2.5 | 3.0 |
| p 8 | 3.0 | 4.7 | 2.4 | 2.8 | 2.0 | 3.2 |
| % Total Levels of Viral Proteins | (100) | (96.6) | (100) | (63) | (100) | (54) |

[a]MJY-alpha cultures were treated with PTT.119, washed and labeled with 35S—methionine (Drug 0-1); chased with labeling [medium (Day 1-2) and relabeled with $^3$H—Leucine on day 6 for 24 hr spent supernatants were harvested ondays 1, 2 and 7, and MMTV purified as described in materials and methods. Percentages are based on quantitation of radioactivity associated with MMTV polypeptides separated by SDS-PAGE. The results are the age of 3 experiments.

In addition, the level of the virion core protein, p24, was again depressed within 24 hours of treatment and throughout the one week examination period. The levels of the other MMTV polypeptides were not significantly affected including the glycoproteins gp60 and gp37.7/33.

EXPERIMENTAL EXAMPLE 20

EFFECTS OF LONG-TERM EXPOSURE TO PTT.119

MJY-alpha cells were exposed to sublethal doses of PTT.119 for prolonged periods to ascertain whether constant tripeptide treatment affected MMTV production. PTT.119 at 0.15, 1.5 and 7.5 uM was continually included in the culture medium for 10 to 13 cell culture passages over a 5 month period. The growth rates of these treated cells were diminished resulting in their subculture every 1.5 to 2 weeks compared to the weekly passage of the untreated parental cells. The level of MMTV production by the confluent monolayers was monitored by ELISA during this period. As shown in Table 15, the levels of extracellular MMTV decreased with PTT.119 treatment and were less than 50% compared to control cells after 10 in vitro passages.

TABLE 15

MMTV PRODUCTION BY CULTURES CONTINUALLY TREATED WITH PTT.119

| PTT.119 (uM) | ug MMTV protein/150 cm$^2$ culture[a] Cell culture passage | | |
|---|---|---|---|
| | 1 | 5-6 | 9-10 |
| 0[b] | 20.32 | 20.32 | 20.32 |
| 0.15 | 17.4 | 16.8 | 9.52 |
| 1.5 | — | 15.9 | 7.5 |
| 7.5 | — | 11.8 | 8.3 |

[a]MJY-alpha cell cultures were continuously treated with PTT.119 by inclusion of 0.15, 1.5, and 7.5 uM tripeptide in the culture medium. Cell layers were not stimulated with hydrocortisone before or during virus collection. Levels of MMTV protein produced were determined by the ELISA method described in Materials and Methods. The values represent the average of 4-6 determinations.
[b]Levels of MMTV from untreated cultures determined by ELISA were similar among the experiments and were pooled to yield a single value; the range of values was 16.6–24.7 ug MMTV protein.

The polypeptide composition of the virions were also examined during the 10th passage of the cells in 0.15 and 7.5 uM PTT.119 and the 13th passage in 1.5 uM tripeptide. NaDodSO$_4$-PAGE of purified MMTV from cultures labeled with $^{35}$S-methionine for 24 hours again revealed depressions in the level of p24 in the extracellular virions. The relative contribution of p24 in the virions was 54%, 74% and 65% of control level in MMTV from cultures treated with 0.15, 1.5 and 7.5 uM PTT.119, respectively.

What is claimed is:

1. A method for interfering with B-type retrovirus replication comprising: exposing host cells infected by the virus to a therapeutically effective dose of a tripeptide compound of from 1.5 to 15 uM in a cell medium surrounding the host cells and in contact with said host cells for 24 to 48 hours, wherein the tripeptide compound is selected from the group consisting of:
   (a) 3-(p-fluorophenyl)-L-alanyl-3-[m-bis(2-chloroethyl)aminophenyl]-L-alanyl-L-methionine
   (b) 3-[m-bis(2-chloroethyl)aminophenyl]-L-alanyl-3-(p-fluorophenyl)-L-alanyl-L-methionine
   (c) 3-(p-fluorophenyl)-L-alanyl-L-methionyl-3-[m-bis(2-chloroethyl)aminophenyl]-L-alanine
   (d) 3-[m-bis(2-chloroethyl)aminophenyl]-L-alanyl-L-methionyl-3-(p-fluorophenyl)-L-alanine
   (e) L-methionyl-3-(p-fluorophenyl)-L-alanyl-3-[m-bis(2-chloroethyl)aminophenyl]-L-alanine
   (f) L-methionyl-3-[m-bis(2-chloroethyl)aminophenyl]-L-alanyl-3-(p-fluorophenyl)-L-alanine, and wherein the therapeutically effective dose of the tripeptide compound is below a lethal dose for the host cells.

2. The method according to claim 1, wherein the tripeptide compound is 3-(p-fluorophenyl)-L-alanyl-3-[m-bis(2-chloroethyl)aminophenyl]-L-alanyl-L-methionine ethyl ester hydrochloride.

3. The method according to claim 2, wherein the virus is a B-type mouse mammary tumor virus.

4. The method according to claim 3, wherein the host cells are MJY-alpha murine mammary cells.

5. The method according to claim 4, wherein exposing the host cells to the tripeptide compound is in vitro.

6. The method according to claim 4, wherein said therapeutically effective dose is from 1.5 to 15 uM of 3-(p-fluorophenyl)-L-alanyl-3-[m-bis(2-chloroethyl)aminophenyl]-L-alanyl-L-methionine ethyl ester hydrochloride present in said cell medium surrounding the host cells and in contact with said host cells for 24 to 48 hours.

7. The method according to claim 4, wherein the host cells are administered with multiple therapeutically effective doses of 3-(p-fluorophenyl)-L-alanyl-3-[m-bis(2-chloroethyl)aminophenyl]-L-alanyl-L-methionine ethyl ester hydrochloride.

* * * * *

UNITED STATES PATENT AND TRADEMARK OFFICE
CERTIFICATE OF CORRECTION

PATENT NO. : 4,740,501
DATED : April 26, 1988
INVENTOR(S) : DeBarbieri et al.

It is certified that error appears in the above-identified patent and that said Letters Patent is hereby corrected as shown below:

Title page, item:

[73] Assignee: PROTER S.p.A., OPERA ITALY, should be inserted after item [76].

Signed and Sealed this

Sixth Day of July, 1993

Attest:

MICHAEL K. KIRK

Attesting Officer	Acting Commissioner of Patents and Trademarks